(12) United States Patent
Ally et al.

(10) Patent No.: US 11,129,524 B2
(45) Date of Patent: Sep. 28, 2021

(54) METHODS AND APPARATUS TO MEASURE FAST-PACED PERFORMANCE OF PEOPLE

(71) Applicant: S2 Cognition, Inc., Nashville, TN (US)

(72) Inventors: Brandon Ally, Nashville, TN (US); Scott Wylie, Brentwood, TN (US)

(73) Assignee: S2 COGNITION, INC., Nashville, TN (US)

( * ) Notice: Subject to any disclaimer, the term of this patent is extended or adjusted under 35 U.S.C. 154(b) by 663 days.

(21) Appl. No.: 15/801,166

(22) Filed: Nov. 1, 2017

(65) Prior Publication Data
US 2018/0055433 A1     Mar. 1, 2018

Related U.S. Application Data

(63) Continuation of application No. PCT/US2016/035915, filed on Jun. 3, 2016.
(Continued)

(51) Int. Cl.
*A61B 5/00*        (2006.01)
*A61B 3/02*        (2006.01)
(Continued)

(52) U.S. Cl.
CPC .................. *A61B 3/02* (2013.01); *A61B 5/16* (2013.01); *A61B 5/162* (2013.01); *A61H 5/00* (2013.01); *A61H 2201/5046* (2013.01)

(58) Field of Classification Search
CPC ........ G06N 20/00; G16H 40/20; A61B 5/165; A61B 5/4064; A61B 5/7275; A61B 3/113;
(Continued)

(56) References Cited

U.S. PATENT DOCUMENTS

| 5,883,692 A | * | 3/1999 | Agonis | ................... | E04C 2/292 |
| | | | | | 351/224 |
| 7,294,107 B2 | * | 11/2007 | Simon | ...................... | A61B 5/16 |
| | | | | | 600/300 |

(Continued)

FOREIGN PATENT DOCUMENTS

WO       0205247       1/2002

OTHER PUBLICATIONS

Jesus Cespon et al: "Electrophysiological Correlates of Amnestic Mild Cognitive Impairment in a Simon Task," PLOS One, vol. 8, No. 12, Dec. 5, 2013, p. e81506, XP055550795, DOI: 10.1371/journal.pone.0081506.
(Continued)

*Primary Examiner* — May A Abouelela
(74) *Attorney, Agent, or Firm* — FisherBroyles, LLP; John Shimmick

(57) ABSTRACT

The present disclosure provides improved methods and apparatus for evaluation of an individual's cognitive performance in a fast-paced, visually dynamic environment. The apparatus may comprise a display configured to present a plurality of stimuli to the subject, and a processor coupled to the display, the processor comprising instructions to determine a subject's visual perceptual skills, memory and learning skills, and response command and control skills. The methods and apparatus described herein can evaluate key cognitive processes that underlie split-second decision-making in visually dynamic environments. The results can provide comparison of cognitive skills across individuals performing in a specific environment, as well as evaluations of more targeted sets of cognitive processes for specific positions in an environment that might require unique sets of skills.

37 Claims, 29 Drawing Sheets

Related U.S. Application Data

(60) Provisional application No. 62/171,336, filed on Jun. 5, 2015.

(51) Int. Cl.
*A61B 5/16* (2006.01)
*A61H 5/00* (2006.01)

(58) Field of Classification Search
CPC ....... A61B 5/1118; A61B 5/4088; A61B 3/02; A61B 5/162; A61B 5/16; A61H 5/00
USPC ................................. 600/300, 558; 434/236
See application file for complete search history.

(56) References Cited

U.S. PATENT DOCUMENTS

| | | | | |
|---|---|---|---|---|
| 7,540,615 | B2* | 6/2009 | Merzenich | G09B 7/04 351/203 |
| 7,556,604 | B2* | 7/2009 | Murata | A61B 5/16 600/558 |
| 8,202,095 | B2* | 6/2012 | Shankle | G09B 19/00 434/236 |
| 8,215,961 | B2* | 7/2012 | Merzenich | G09B 7/02 434/236 |
| 8,760,395 | B2* | 6/2014 | Kim | G06F 3/011 345/156 |
| 8,979,263 | B2* | 3/2015 | Lawton | G09B 19/00 351/200 |
| 8,979,540 | B2* | 3/2015 | Duffy | A61B 5/162 434/236 |
| 9,308,446 | B1* | 4/2016 | Merzenich | G09B 19/00 |
| 9,940,844 | B2* | 4/2018 | Gazzaley | G09B 5/02 |
| 10,311,744 | B2* | 6/2019 | Zhang | A61B 5/4088 |
| 2003/0032866 | A1* | 2/2003 | Winter | A61B 5/16 600/300 |
| 2003/0073885 | A1 | 4/2003 | Theodoracopulos | |
| 2003/0109800 | A1 | 6/2003 | Polat | |
| 2004/0049124 | A1* | 3/2004 | Kullok | A61B 5/163 600/558 |
| 2005/0187436 | A1 | 8/2005 | Doniger | |
| 2005/0273017 | A1 | 12/2005 | Gordon | |
| 2007/0218440 | A1 | 9/2007 | Delahunt | |
| 2010/0217097 | A1* | 8/2010 | Chen | A61B 5/16 600/301 |
| 2011/0105855 | A1* | 5/2011 | Johnson | G01N 33/6896 600/300 |
| 2011/0118559 | A1* | 5/2011 | Aharonson | A61B 5/162 600/300 |
| 2011/0263946 | A1* | 10/2011 | el Kaliouby | G06K 9/00335 600/300 |
| 2011/0301431 | A1* | 12/2011 | Greicius | G06T 7/0012 600/300 |
| 2012/0059282 | A1* | 3/2012 | Agichtein | A61B 3/113 600/587 |
| 2012/0075586 | A1 | 3/2012 | Kirschen | |
| 2012/0154745 | A1 | 6/2012 | Yoo | |
| 2013/0090562 | A1* | 4/2013 | Ryan | A61B 5/165 600/473 |
| 2013/0338483 | A1* | 12/2013 | Neuvonen | A61B 5/4064 600/411 |
| 2014/0066802 | A1* | 3/2014 | Kaula | A61B 5/16 600/554 |
| 2014/0142439 | A1* | 5/2014 | French | A61B 5/0077 600/483 |
| 2014/0154651 | A1* | 6/2014 | Stack | A61B 5/163 434/236 |
| 2014/0168606 | A1* | 6/2014 | Berry | G16H 40/67 351/223 |
| 2014/0243652 | A1* | 8/2014 | Pashko | A61B 5/04001 600/409 |
| 2014/0249447 | A1* | 9/2014 | Sereno | A61B 5/7475 600/558 |
| 2014/0336539 | A1* | 11/2014 | Torres | A61B 5/40 600/595 |
| 2014/0343450 | A1* | 11/2014 | Stack | A61B 5/4833 600/558 |
| 2015/0011864 | A1* | 1/2015 | Reisberg | A61K 31/343 600/410 |
| 2015/0051508 | A1* | 2/2015 | Ghajar | A61B 5/163 600/558 |
| 2015/0126899 | A1 | 5/2015 | Ghajar | |
| 2015/0164418 | A1* | 6/2015 | Johnson | A61B 5/4884 434/236 |
| 2015/0187227 | A1* | 7/2015 | Zhang | A61B 5/72 434/236 |
| 2015/0196232 | A1* | 7/2015 | Mitsi | G09B 5/02 600/595 |
| 2015/0216414 | A1* | 8/2015 | Wood | A61B 5/7475 600/303 |
| 2015/0282705 | A1* | 10/2015 | Avital | A61B 3/113 600/301 |
| 2015/0297108 | A1* | 10/2015 | Chase | A61M 21/00 600/9 |
| 2016/0007899 | A1* | 1/2016 | Durkee | A61B 5/04012 600/544 |
| 2016/0038049 | A1* | 2/2016 | Geva | A61B 5/7267 600/544 |
| 2016/0073945 | A1* | 3/2016 | Fine | G06K 9/00355 600/558 |
| 2016/0073947 | A1* | 3/2016 | Anderson | A61B 5/7282 600/301 |
| 2016/0310059 | A1* | 10/2016 | Faubert | A61B 5/4088 |

OTHER PUBLICATIONS

Rasa Gulbinaite et al.: "Fronto-parietal network oscillations reveal relationship between working memory capacity and cognitive control," Frontiers in Human Neuroscience, vol. 8, Sep. 30, 2014 XP055550788: DOI: 10.3389/fnhum.2014.00761.

Robert W Proctor: "Playing the Simon game: Use of the Simon task for investigating human information processing," Acta Psychologica, vol. 136, No. 2, Feb. 1, 2011, pp. 182-188, XP055550742, ISSN: 0001-6918, DOI: 10.1016/j.actpsy.2010.06.010.

Miriam Spering et al: "Keep your eyes on the ball: smooth pursuit eye movements enhance prediction of visual motion", Journal of Neurophysiology, vol. 105, No. 4, Apr. 1, 2011 (Apr. 1, 2011), pp. 1756-1767, XP055515864, US ISSN: 0022-3077, DOI: 10.1152/jn. 00344.2010.

NintenDaan: "[eShop EU] Brain Training (DS VC)—First Look", Youtube, Jun. 16, 2014 (Jun. 16, 2014), p. 1, XP054978777. Retrieved from the Internet: URL:https://www.youtube.com/watch?v=KtzB5cCuBu8 [retrieved on Oct. 12, 2018].

Wouter Van Den Bos: "Better than expected or as bad as you thought? The neurocognitive development of probabilistic feedback processing", Frontiers in Human Neuroscience, vol. 3, Jan. 1, 2009 (Jan. 1, 2009), XP055517332, DOI: 10.3389/neuro.09.052.2009.

"Perceptual learning in motion discrimination that generalizes across motion directions", Proceedings of the National Academy of Sciences of the United States of America, vol. 96, No. 24, Nov. 23, 1999 (Nov. 23, 1999), pp. 14085-14087, XP055515596, ISSN: 0027-8424, DOI: 10.1073/pnas.96.24.14085.

International Search Report and Written Opinion for International Application No. PCT/US2016/035915, 13 pages (dated Aug. 30, 2016).

Kim, Yong-Guk, et al., "Trajectory Interpretation by Supplementary Eye Field Neurons During Ocular Baseball," J. Neurophysiol 94:1385-1391 (2005).

Shaw, T.H., et al., "Event-related cerebral hemodynamics reveal target-specific resource allocation for both "go" and "no-go" response-based vigilance tasks," Brain and Cognition, 82:265-273 (2013).

Smith, A.P., et al., "An investigation of the effects of the common cold on simulated driving performance and detection of collisions: a laboratory study," BMJ Open, vol. 2, No. 4, Jan. 1, 2012, p. e001047, XP055667838, ISSN: 2044-6055, DOI: 10.1136/bmjopen-2012-001047.

(56) References Cited

OTHER PUBLICATIONS

Ally, Brandon A., et al., "Pattern Separation and Pattern Completion in Alzheimer's Disease: Evidence of Rapid Forgetting in Amnestic Mild Cognitive Impairment," Hippocampus, 23(12):1246-1258 (Dec. 2013).
Bares, Martin, et al., "Predictive Motor Timing Performance Dissociates Between Early Diseases of the Cerebellum and Parkinson's Disease," Cerebellum, 9:124-135 (2010).
Claassen, Daniel O., et al., "The Risky Business of Dopamine Agonists in Parkinson Disease and Impulse Control Disorders," Behav. Neurosci., 125(4):492-500 (Aug. 2011).
Fumarola, Antonia, et al., "The Spatial Representation of Angles," Perception, 45(11):1320-1330 (2016).
Haladjian, Harry H., et al., "A snapshot is all it takes to encode object locations into spatial memory," Vision Research, 107:133-145 (2015).
Kihara, Ken, et al., "Usability of liquid crystal displays for research in the temporal characteristics of perception and attention," Behavior Research Methods, 42(4):1105-1113 (2010).
Landy, Kelly M., et al., "Motion discrimination in dementia with Lewy bodies and Alzheimer disease," Neurology, 85_1376-1382 (Oct. 20, 2015).
Leskovec, J., Rajaraman A., and Ullman, J.D., "Mining of Massive Datasets: 7.2. Hierarchical Clustering," pp. 245-254 (2014).
Miyake, Akira, et al., "The Nature and Organization of Individual Differences in Executive Functions: Four General Conclusions," Curr Dir Psychol Sci., 21(1):8-14 (Feb. 2012).
Molitor, Robert J., et al., "Eye Movements in Alzheimer's Disease," J Alzheimers Dis., 44(1):1-12 (2015).
Port, Nicholas L., et al., "Motor Cortical Activity during Interception of Moving Targets," Journal of Cognitive Neuroscience, 13(3):306-318 (2001).
Proctor, Robert W., et al., "Stimulus-Response Compatability for Moving Stimuli: Perception of Affordances or Direction Coding?" Journal of Experimental Psychology: Human Perception and Performance, 19(1):81-91 (1993).
Robertson, C., et al., "Motor set in Parkinson's disease," Journal of Neurology, Neurosurgery, and Psychiatry, 53:583-592 (1990).
Shapiro, Kimron L., et al., "The attentional blink," Trends in Cognitive Sciences, 1(8):291-296 (Nov. 1997).
Tolleson, Christopher M., et al., "Dysrhythmia of Timed Movements in Parkinson's disease and Freezing of Gait," Brain Res., 1624:222-231 (Oct. 22, 2015).
Treisman, Anne, "Perceptual Grouping and Attention in Visual Search for Features and for Objects," Journal of Experimental Psychology: Human Perception and Performance, 8(2):194-214 (1982).
Van Den Wildenberg, Wery P. M., et al., "Overriding Actions in Parkinson's Disease: Impaired Stopping and Changing of Motor Responses," Behavioral Neuroscience, 131(5):372-384 (2017).
Van Wouwe, Nelleke C., et al., "Dopamine Selectively Modulates the Outcome of Learning Unnatural Action—Valence Associations," J. Cogn. Neurosci., 29(5):816-826 (May 2017).
Watson and Pelli, "QUEST: A Bayesian Adaptive Psychometric Method," Perception & Psychophysics, 33(2):113-120 (1983).
Wolfe, Jeremy M., et al., "Multiple object juggling: Changing what is tracked during extended multiple object tracking," Psychonomic Bulletin & Review, 14(2):344-349 (2007).
Wylie, S.A., et al., "The effect of Parkinson's disease on interference control during action selection," Neuropsychologia, 47(1):145-157 (Jan. 2009).
Wylie, Scott A., et al., "Subthalamic nucleus stimulation influences expression and suppression of impulsive behaviour in Parkinson's disease," Brain, 133:3611-3624 (2010).
Coull, Jennifer T., et al., "Using time-to-contact information to assess potential collision modulates both visual and temporal prediction networks," Front. Hum. Neurosci. 2(10):1-12 (Sep. 2008).
Yang, Shun-nan, et al., "Contrasting the roles of the supplementary and frontal eye fields in ocular decision making," Journal of Neurophysiology, vol. 111(12):2644-2655 (Jun. 2014).

\* cited by examiner

METHODS AND APPARATUS TO MEASURE FAST-PACED PERFORMANCE OF PEOPLE

CROSS-REFERENCE

The present application is a continuation of International Application No. PCT/US2016/035915, filed Jun. 3, 2016, published as WO 2016/197063, on Dec. 8, 2016, which claims the benefit of U.S. Provisional Patent Application No. 62/171,336, filed Jun. 5, 2015, the entire contents of which are incorporated herein by reference.

BACKGROUND OF THE INVENTION

Prior methods and apparatus for measuring a person's ability to respond to a fast paced environment can be less than ideal in at least some respects. Many people are placed in fast paced environments in which an individual's ability to think, react, and perform quickly can be critical. Examples of fast paced environments include sports, law enforcement, firefighters and the military. For example, in less than a few seconds and often in fractions of a second, a football player can be required to assess an opposing team and make decisions and respond to opposing players. As several players and visual stimuli are involved, the individual's ability to recognize patterns, remember patterns, and respond to the actions of the other team can be critical. Similarly, law enforcement and military personnel may need to make critical decisions and respond within fractions of a second to a few seconds. Prior methods and apparatus to measure an individual's ability to respond to fast paced situations may not detect cognitive processes operating in these timescales or adequately isolate and measure specific processes or individual differences in these processes. Although advances in cognitive neuroscience have been made, prior neurological and neuropsychological assessments of individuals can provide a less than ideal assessment of an individual's ability to perform cognitively in a fast paced environment.

There is an unmet need for improved methods and apparatus to assess an individual's ability to perform in a fast past environment. Prior athletic performance metrics such as time running a distance or paper-and-pencil tests provide inadequate assessment of cognitive abilities demanded of the player during play. For example, teams of the National Football League (NFL) have used the Wonderlic test, a paper-and-pencil measure of intelligence and football knowledge, which has been demonstrated to provide minimal value predicting successful performance on the football field. Examples include Terry Bradshaw, Dan Marino, and Jim Kelly, all of whom have been inducted into the American football hall of fame but performed poorly on the Wonderlic test, e.g. 16, 15, and 15, respectively, out of a possible 50 points. Professional sports teams, law enforcement, fire departments and military organizations spend vast amounts of time and money attempting to evaluate intellectual abilities of candidates to predict success in fast-paced environments, but with less than ideal results.

In light of the above, improved methods and apparatus are needed to provide an improved assessment of an individual's cognitive performance in fast-paced environments.

SUMMARY OF THE INVENTION

The present disclosure provides improved methods and apparatus for evaluation of an individual's performance in a fast-paced, visually dynamic environment. The methods and apparatus described herein can evaluate key cognitive processes that underlie split-second decision-making in visually dynamic environments. The methods and apparatus may be used to assess an individual's decision-making ability that links a visual input to a motor output, which can involve three key sets of processes: visual perception skills, or the detection, tracking, and attending to what and where things are in the visual environment; memory and learning skills, or the recognition of visual information and translation of the information into pre-determined or new effective action decisions; and response command and control, or the effective starting, stopping, and redirecting of an individual's motor system as things change dynamically in the visual environment. The evaluation can measure several core processes, but is highly flexible and can be tailored to specific environments demanding fast-paced cognition. The results can provide comparison of cognitive skills across individuals performing in a specific environment, as well as evaluations of more targeted environments that might require unique sets of cognitive skills.

In one aspect, an apparatus to measure a subject comprises a display to present a plurality of stimuli to the subject and a processor coupled to the display. The processor comprises instructions to determine a visual perception of the subject, a memory and learning of the subject, and a command and control of the subject. The plurality of stimuli may comprise stimuli to measure visual perception of the subject, stimuli to measure memory and learning of the subject and stimuli to measure command and control of the subject.

The stimuli to measure visual perception of the subject may comprise a plurality of stimuli to evaluate one or more of visual, visuoperceptual, or visual attention brain circuitries. The plurality of stimuli may comprise stimuli to evaluate one or more brain circuitries of an occipital cortex, fusiform gyrus, dorsal visual pathway, ventral visual pathway, parietal cortex, or visual association cortex of the subject.

The stimuli to measure memory and learning of the subject may comprise a plurality of stimuli to evaluate one or more of explicit memory of the subject, implicit memory of the subject, or procedural memory of the subject. The plurality of stimuli may comprise stimuli to evaluate one or more brain circuitries of a hippocampus, parietal cortex, mesial temporal lobes, frontal lobes, or basal ganglia of the subject.

The stimuli to measure command and control of the subject may comprise a plurality of stimuli to evaluate one or more executive cognitive control systems of the subject. The plurality of stimuli may comprise stimuli to evaluate one or more brain circuitries of a dorsolateral and ventrolateral prefrontal cortex, motor cortex, premotor cortex, pre-supplementary motor cortex, parietal cortex, cingulate cortex, or subcortical basal ganglia structures of the subject. The processor may comprise instructions to measure an ipsilateral response to a stimulus shown on a first side of the display and a contralateral response to the stimulus shown on a second side of the display, wherein the first side may be separated from the second side with a midline of the display when a midline of the subject is aligned with the midline of the display. A right stimulus may be presented on a right side of the display and the subject may respond with a right hand to measure the ipsilateral response, and a left stimulus may be presented on a left side of the display and the subject may respond with the right hand to measure the contralateral response. A time from presentation of the right stimulus to the subject providing an input with the right hand may determine the ipsilateral response, and a time from presentation of the left stimulus to the subject providing an input with the right hand may determine the contralateral response. A left stimulus may be presented on a left side of the display and the subject may respond with a left hand to measure the ipsilateral response, and a right stimulus may be presented on a right side of the display and the subject may respond with the left hand to measure the contralateral response. A time from presentation of the left stimulus to the subject providing an input with the left hand may determine the ipsilateral response, and a time from presentation of the right stimulus to the subject providing an input with the left hand may determine the contralateral response.

The processor may comprise instructions to provide an assessment task configured to measure one or more of the following: a speed and accuracy of the subject at locating a target in a distracting visual environment; an ability of the subject to track multiple moving targets simultaneously; a speed at which the subject disengages and shifts visual attention to a new target; an ability of the subject to detect a direction of movement of a target amid visual distraction and chaos; an ability of the subject to estimate a speed and trajectory of a moving visual target; an ability of the subject to rapidly discriminate a motion of a visual target.

The processor may comprise instructions to provide an assessment task configured to measure one or more of the following: an ability of the subject to recognize and discriminate complex visual patterns; an ability of the subject to detect subtle changes in a visual scene; an ability of the subject to learn how to react to new visual information based on probabilistic feedback; a speed and accuracy of the subject at selecting an optimal response for a situation as response options increase in number; a speed and accuracy of the subject at translating visual motion into action based on context.

The processor may comprise instructions to provide an assessment task configured to measure one or more of the following: an ability of the subject to regulate and optimize a speed and accuracy of reactions; an ability of the subject to prevent and recover from initial action impulses; an ability of the subject to minimize performance costs when faced with visual distractions; an ability of the subject to control timing of reactions to rapidly moving visual targets; an ability of the subject to regulate a decision to act or withhold action, based on whether a moving visual target is predicted to intercept or avoid a point in space.

The processor may comprise instructions to provide an assessment task configured to measure one or more of the following: an ability of the subject to encode and maintain representations of target locations in a working memory of the subject; a speed of initiation of action and inhibition of action by the subject in response to visual cues in an environment of the subject; an efficiency of the subject of learning a repeated sequence of motor actions, costs to performance of the subject when the learned sequence is disrupted, and an ability of the subject to re-acquire the sequence upon reinstatement of the learned sequence after disruption; an accuracy of externally cued rhythmic motor timing of the subject and rhythmic motor timing of the subject that is maintained based on an internal, mental representation of the timing; a preference of the subject for making relatively risky decisions or relatively cautious decisions when rewards are at stake; an accuracy of the subject in predicting how a moving target will angle off of stationary objects; an accuracy of the subject in estimating a spatial angle; an ability of the subject to predict an initial reaction to intersect a moving target and an ability of the subject to adjust the prediction and reaction when the target unexpectedly changes direction; an ability of the subject to suppress memories and limit intrusion of the memories on and interference of the memories with subsequent performance of the subject.

The apparatus may further comprise an input device responsive to one or more hands of the subject, wherein the input device is coupled to the processor. The processor may comprise instructions to provide the plurality of stimuli on the display within no more than about 20 ms of an instruction to show the stimuli on the display, and measure a subject input provided to the input device within no more than about 20 ms of the subject providing the subject input to the display. The instructions may comprise instructions of an application downloaded from a network, wherein the display may comprise a display of a computing device, and wherein the input device may comprise an input device coupled to the computing device.

In another aspect, a method of evaluating performance of a subject comprises providing a display to present a plurality of stimuli to the subject. The method further comprises providing a processor coupled to the display, the processor comprising instructions to determine a visual perception of the subject, a memory and learning of the subject, and a command and control of the subject. The method further comprises receiving, using an input device coupled to the processor, input provided by the subject in response to the plurality of stimuli.

In another aspect, disclosed herein is a method comprising providing any apparatus as described herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The apparatus and methods described herein can measure cognitive processes that are important in making split-second decisions in fast-paced, visually dynamic environments. The ability to effectively make and act on such split-second decisions can serve as an important metric for the likelihood of successful performance of an individual in such environments. For example, elite athletes across a range of sports (e.g., football, basketball, hockey, baseball), military personnel (e.g., marines, soldiers, airmen, sailors), police force, and fire fighters often make decisions in fractions of seconds to a few seconds. The performance evaluation apparatus described herein can evaluate key cognitive processes that underlie such split-second decisions in fast-paced and visually dynamic environments. Key cognitive processes may include processing chaotic and dynamic visual information rapidly, recognizing visual patterns and cues rapidly and selecting appropriate reactions efficiently, and effectively commanding and controlling actions and reactions as events unfold. The evaluation can measure several core processes, but is highly flexible and can be tailored to specific environments (e.g., baseball versus football cognition). The results can provide comparison of cognitive skills across individuals performing in a specific environment, as well as evaluations of more targeted sets of cognitive processes for skilled performances that might require unique sets of skills (e.g., quarterbacks versus cornerbacks, army rangers versus navy seals, etc.).

The evaluation apparatus can assess an individual's ability to process a visual input and produce a motor output in visually dynamic environments. The successful processing of a visual input to produce a motor output can involve three key sets of processes. First, a high level of visual and visuoperception skills is often needed to detect, track, and attend to what and where things are in the visual environment. Second, memory and learning skills are often necessary to rapidly recognize visual information and translate the information into effective action decisions. Finally, command and control skills are often needed to effectively control the speed and accuracy of reactions, control impulsive reactions, regulate the timing of actions, and rapidly redirect the individual's motor system as things change dynamically in the visual environment.

Figure 1:
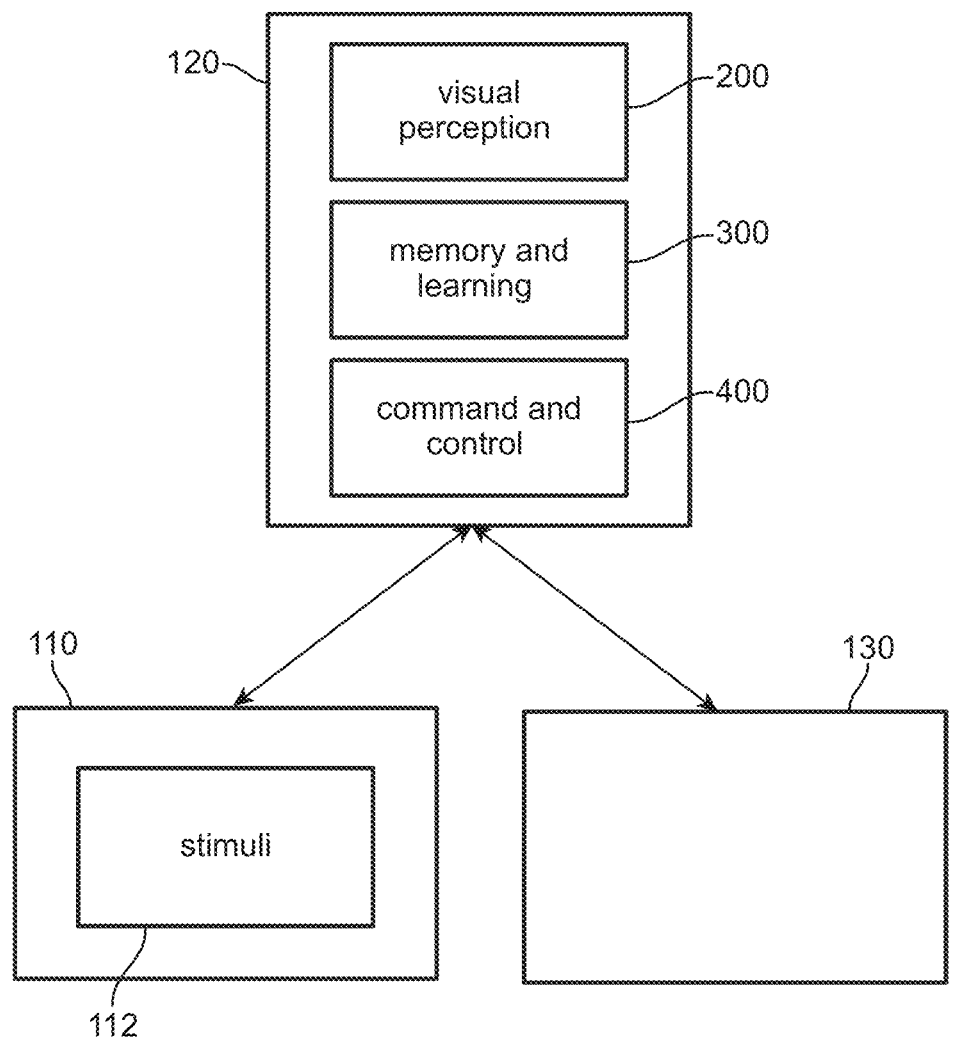
FIG. 1 shows a schematic diagram of an evaluation apparatus, in accordance with embodiments.

FIG. 1 shows a schematic diagram of an evaluation apparatus 100, in accordance with embodiments. The evaluation apparatus comprises a display 110 and a processor 120 coupled to the display. The display may be configured to present a plurality of stimuli 112 to the subject. The processor may comprise instructions to determine a visual perception 200 of a subject, a memory and learning 300 of the subject, and a command and control 400 of the subject. The plurality of stimuli may comprise stimuli to measure the visual perception of the subjection, stimuli to measure memory and learning of the subject, and stimuli to measure command and control of the subject. The instructions of the processor may comprise instructions to provide the stimuli on the display. The processor and the display may be configured such that the stimuli are provided to the display within no more than about 20 ms, for example, 10 ms, or 5 ms of an instruction to show the stimuli on the display.

Figure 2:
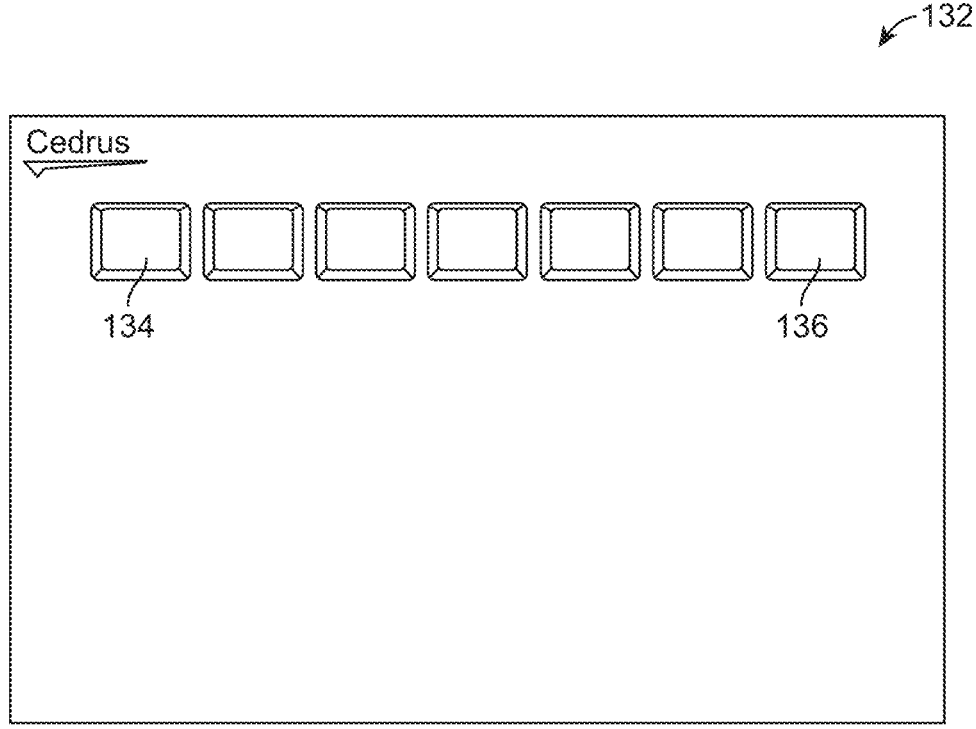
FIG. 2 shows an exemplary response pad suitable for incorporation with the evaluation apparatus of FIG. 1.

The evaluation apparatus may further comprise an input device 130 responsive to one or more hands of the subject, wherein the input is coupled to the processor. The input device may comprise one or more of response pad, a computer mouse or track pad, and a computer keyboard. The instructions of the processor may comprise instructions to detect and/or analyze one or more subject inputs to the input device. The processor and the input device may be configured such that the processor can detect the subject input within a few ms of the subject providing the input to the input device. The input device may have a reaction time resolution of no more than about 20 ms, for example, 10 ms, or 5 ms. For example, the input device can comprise a keyboard with a universal serial bus (USB) connection, having a reaction time resolution of about 10-15 ms. Alternatively or in combination, the input device may a reaction time resolution of less than 5 ms, in order to determine the reaction speed of the subject with a high level of resolution. For example, the input device may comprise a RB Series Desktop Response Pad manufactured by Cedrus Corp. (San Pedro, Calif.) or a similar response pad, configured to have a reaction time resolution of about 2-3 ms. FIG. 2 shows an exemplary response pad 132 suitable for incorporation with the evaluation apparatus 100. A response pad often comprises a plurality of buttons, such as the left outside button 134, right outside button 136, and additional buttons in between. In many embodiments, only one or two buttons of the plurality of buttons may be used by the subject to provide input; the one or two buttons may often be the buttons placed in locations easiest for the subject to reach, such as the outside buttons 134 and 136 of the response pad 132.

The instructions of the processor to determine the visual perception, memory and learning, and command and control of a subject may comprise instructions of an application downloaded from a network, such as the Internet. The display may comprise a display of a mobile communication device, wherein the input device comprises an input device coupled to the mobile communication device.

The instructions of the processor to determine the visual perception, memory and learning, and command and control of a subject can comprise instructions to provide a task to be performed by the subject. A task may be designed such that an individual's performance of the task can indicate the level of a specific set of cognitive skills of the individual. The task may comprise a subject responding to the plurality of stimuli presented on the display using an input device, wherein both the display and the input device are coupled to the processor comprising instructions to provide the stimuli and to receive the subject input.

Several exemplary tasks for measuring specific cognitive processes are described in further detail herein. A person of ordinary skill in the art will recognize that the described tasks may be modified in various ways. For example, one or more parameters or steps within a task may be modified, completed in a different order, added, or deleted. Some of the steps within a task may comprise sub-steps. Many of the steps within a task may be repeated as often as beneficial for the evaluation. Further, a combination of two or more tasks may be performed. Some of the tasks may comprise sub-tasks. One or more of the two or more tasks may be repeated as often as beneficial for the evaluation.

Visual Perception

Figure 3:
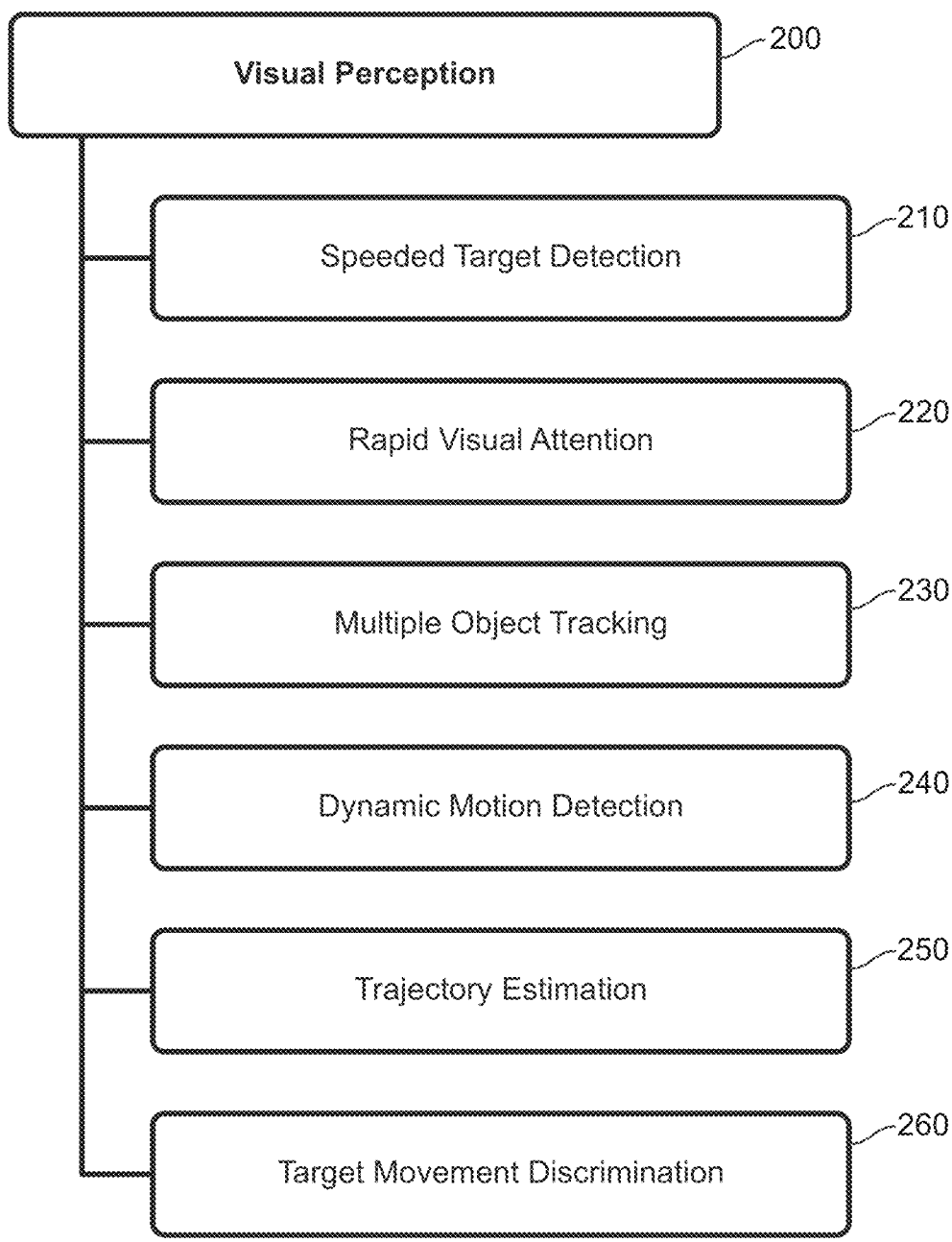
FIG. 3 shows a summary of some exemplary tasks that may be provided by the evaluation apparatus to evaluate cognitive processes related to visual perception.

FIG. 3 shows a summary of some exemplary tasks that may be provided by the evaluation apparatus to evaluate cognitive processes related to visual perception 200. A speeded target detection task 210 may measure a subject's speed and accuracy at locating a target in a distracting visual environment. A rapid visual attention task 220 may measure a subject's ability to track multiple moving targets simultaneously. A multiple object tracking task 230 can measure the speed at which a subject can disengage and shift visual attention to a new target. A dynamic motion detection task 240 can gauge a subject's ability to detect the direction of movement of a target amid visual distraction and chaos. A trajectory estimation task 250 may measure a subject's ability to estimate the speed and trajectory of a moving visual target. A target movement discrimination task 260 can measure a subject's capacity for rapid discrimination of a visual target and its motion. Each of these tasks can be designed and configured to test a specific set of underlying cognitive processes, by providing one or more appropriately designed stimuli and instructing the subject to provide specific input in response to the stimuli. The one or more appropriately designed stimuli may include, for example, a plurality of stimuli to evaluate one or more of visual, visuoperceptual, and visual attention brain circuitries inclusive of the occipital cortex, a fusiform gyrus, a dorsal visual pathway, ventral visual pathway, parietal cortex, or visual association cortex.

Speeded Target Detection

An important component of visual performance in dynamic visual environments is the ability to efficiently search a distracting visual field for a target. This can be a particularly challenging feat as features overlap between distractors and target in the visual environment. The speeded target detection task as described herein can measure individual differences in the efficiency of directing spatial attention in a distracting visual environment to locate a visual target.

Figure 4:
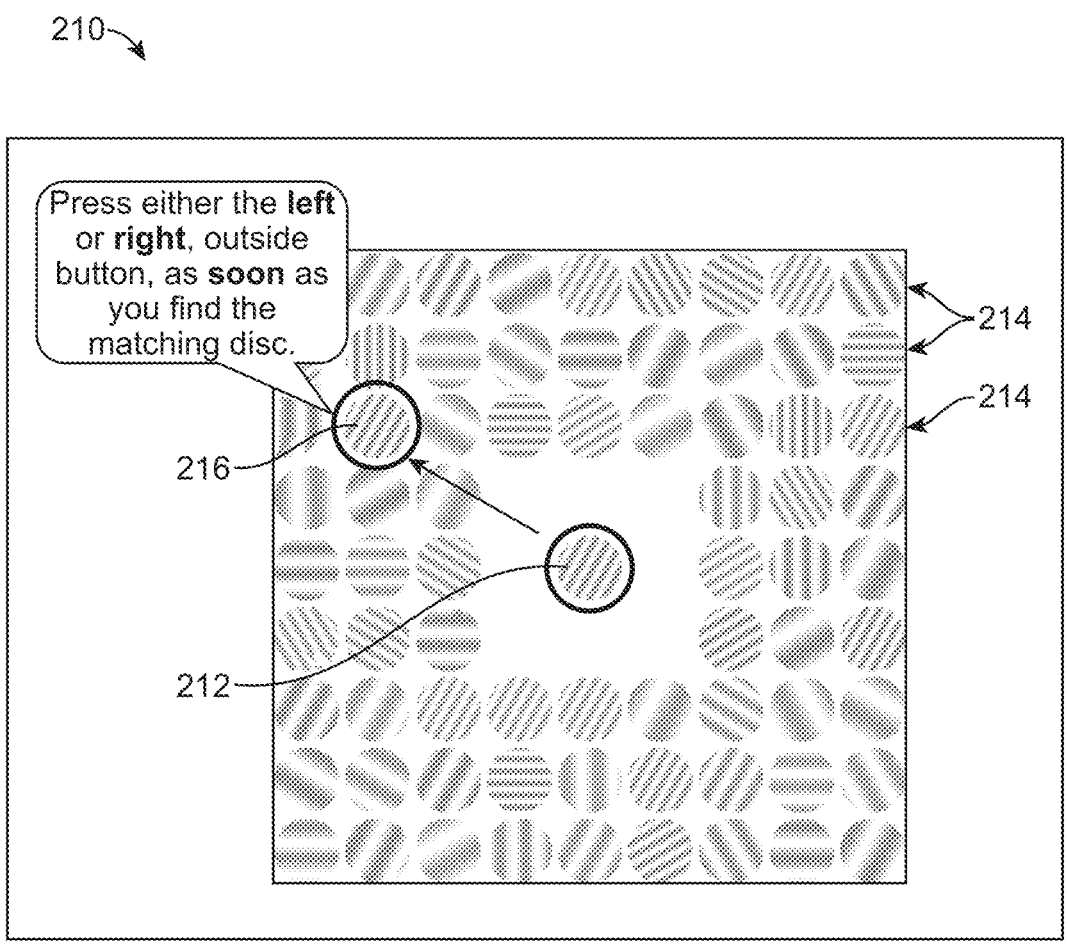
FIG. 4 shows an exemplary screenshot of a speeded target detection task, in accordance with embodiments.

FIG. 4 shows an exemplary screenshot of a speeded target detection task 210 for evaluating the ability to efficiently search a distracting visual field for a target. Subjects may be presented with stimuli comprising a circle 212 in the center of the display screen, the circle being defined by a particular color and design. Three rows of circles 214 may surround the center circle, wherein the surrounding circles share 0, 1 or 2 features with the center circle. For example, the surrounding circles can have various patterns and/or colors, which may be distributed in a random manner among the surrounding circles. One of the surrounding circles can be a perfect match 216 with the center circle. For example, the matching circle 216 and central circle 212 may comprise stripes of the same color and thickness arranged in the same orientation, and/or having any other matching visual characteristics (e.g., same pattern of fading between stripes). In this exemplary embodiment, subjects are instructed to locate the circle in the surrounding circles that perfectly matches the center circle. Subjects are instructed to find the matching circle as quickly and as accurately as possible. This type of "conjunction search" can demand serial shifts of spatial attention along the search array, as is well known in the art. The task instructions, practice trials, and performance trials can take approximately 3 minutes to complete.

The circle stimuli may be comprised of sine-wave gratings spanning 3 degrees visual angle (°) in diameter that are composed of specific color, orientation, and spatial frequency values. The colors can be 12 equidistant coordinates of an imaginary circle positioned around the white point in the 1976 CIE $L^*a^*b^*$ (CIELAB) color space, set to a luminance of $L^*=50$. The orientations may range from 0 to 165 arc-degrees in 15-arc-degree increments. The spatial frequencies may range from 0.4 to 1.85 cycles/° in 0.15 cycle increments. The gratings can be positioned on the coordinates of a 9×9 array spanning 30° across. A "template" grating resembling the search target can appear in the center of this array, and non-targets can appear in all other positions except for the 8 positions surrounding the center position. The target can be defined by randomly selecting a unique combination of color, orientation and frequency on each trial. The 72 non-targets may share 0, 1, or 2 features with the target. The non-target items sharing 1 feature with the target can overlap with the target in color (C), orientation (O), or frequency (F) in equal proportions in the array. The non-target items sharing 2 features with the target can overlap in color-orientation (CO), color-frequency (CF), or orientation-frequency (OF) in equal proportions. A subject can provide an input in response to the stimuli with a single button press on a response pad when the subject detects the matching stimulus. Subsequently, the subject can move a cursor of a mouse to the target, and click the left mouse button to select the stimulus match.

Each trial of the task may begin with a black and white "bull's eye" stimulus appearing in the center of the display screen for about 500 ms. The search array, such as the array of circles 212, 214, and 216, may appear subsequently, and remain visible until the subject presses a button on the response pad indicating that the target has been found. When this button press is detected, a mouse cursor may appear in the center of the screen. The subject may be provided a limited amount of time, for example about 3000 ms, to move the cursor with the mouse over the location of the target and click on it. When a location is clicked, the search array can disappear and the subject may be provided with a blank screen for a short length of time, for example about 1000 ms, before the next trial begins. Failure to click on a valid location in the search array within the allotted time may result in the offset of the search array and a prompt to the subject indicating that the allotted time has expired. Subjects may first complete a practice block of 3 trials. Subsequently, subjects may complete a total of 8 performance trials.

Key dependent measures for the speeded target detection task can comprise the median reaction time of trials when the target was accurately selected ("Correct RT") and the proportion of trials when the target was accurately selected ("Accuracy").

Rapid Visual Attention

Visual attention is known to have temporal constraints so that processing one stimulus (i.e., identifying a letter) consumes resources to an extent that prevents adequate processing of subsequent stimuli for a brief period of time. The two-target rapid serial visual presentation (RSVP) paradigm is well known in the art to reveal individual differences in this refractory period, commonly called the attentional blink.

Figure 5:
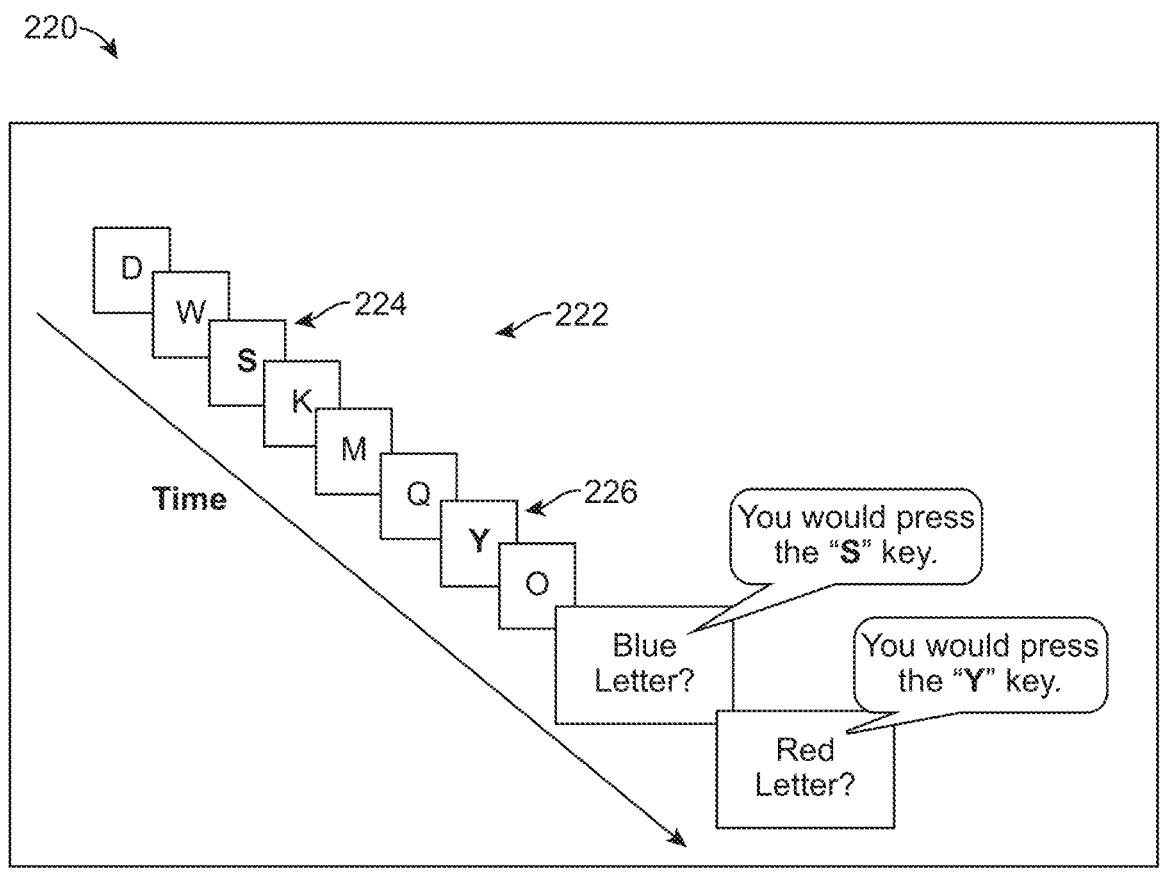
FIG. 5 shows an exemplary screenshot of a rapid visual attention task, in accordance with embodiments.

FIG. 5 shows an exemplary screenshot of a rapid visual attention task 220 for evaluating visual attention in a rapidly changing environment. Subjects may be provided with stimuli comprising a sequence of 13 letters 222 presented at a rate of about 100 ms/per letter. All of the letters can appear in white font except for two letters, one appearing in blue font 224 (letter "S" in FIG. 5) and the other in red font 226 (letter "Y" in FIG. 5). Subjects may be instructed to report the identity of the two letters in the blue and red fonts. The blue letter can be configured to always appear first, but the position of the red letter may be varied with respect to the blue letter. For many individuals, the ability to identify the red letter is most difficult in a time window within a range from about 300 ms to about 500 ms following the blue letter, but the duration and magnitude of this attentional blink can vary among individuals. Thus, this task can capture the temporal resolution of attention when visual information in the environment is changing rapidly. The task instructions, practice trials, and performance trials may take approximately 4 minutes to complete.

The primary stimuli may comprise white letters presented in 40-point Arial font, against a gray background. The target stimuli can be blue and red letters (not equiluminant). Subjects may provide their input using a standard computer keyboard.

At the beginning of the task, subjects may first be shown a central dot for about 500 ms. They may then be shown a sequence of 13 letters at a rate of about 100 ms/letter, followed by a "&" symbol. There may be two colored letters in each sequence, the first colored blue and the second colored red. The first target may appear in temporal positions 3, 4 or 5. The second target may appear after 0-5 intervening letters, establishing lags 1-6. Participants may then be prompted to report the target letters, first entering the identity of the blue letter then the red letter, using the keyboard. Subjects may first complete a practice block of 4 trials, followed by a total of 27 complete performance trials.

Key dependent measures for the rapid visual attention task may comprise a Temporal Attention Index, defined by the following equation:

$$1-(AB\text{slope}+T2\text{cost})$$

where:
ABslope=max(T2|T1)−min(T2|T1)
T2 cost=mean(T1 accuracy)−mean(T2|T1 accuracy), and
T2|T1=the probability of identifying T2 given that T1 was correctly identified Values of this index may range from 1 (superior temporal attention) to 0 (inferior temporal attention). This measure can capture two classic features of the attention blink: (1) superior identification of the first target (T1) over the second target (T2|T1), and (2) low T2|T1 accuracy at short lags compared to long lags. Although this index is agnostic to which level of lag has generated the highest or lowest performance, variability in this measure can reflect low T2|T1 accuracy at short versus long lags.

Multiple Object Tracking

Dynamic visual environments often require the simultaneous tracking of multiple moving visual targets while ignoring the movement of irrelevant visual stimuli. Individuals can differ in their ability to maintain attention to visual targets that are changing dynamically in time and space. The multiple object tracking task described herein can measure individual differences in the capacity for tracking multiple moving visual targets in a chaotic visual environment.

Figure 6:
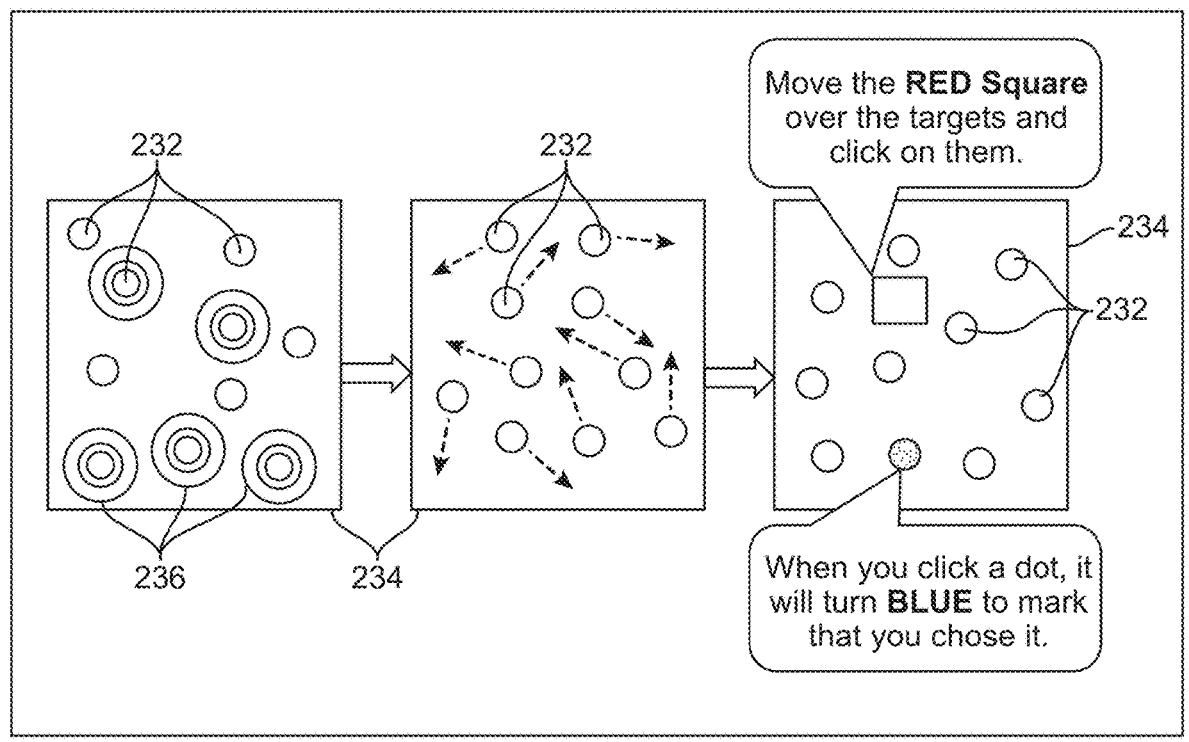
FIG. 6 shows an exemplary screenshot of a multiple object tracking task, in accordance with embodiments.

FIG. 6 shows an exemplary screenshot of a multiple object tracking task 230 for evaluating the ability to maintain attention to rapidly changing visual targets. Subjects may be presented with stimuli comprising about 6-12 identical circular discs 232, randomly dispersed within a large window frame 234 on the display screen. At the beginning of each trial, a certain number of the discs may be highlighted, for example with circles 236 around the discs. The subject may be instructed to track the movements of the highlighted discs. The highlights can then be removed, and all of the discs can start moving randomly for a few seconds and then stop. The subject may then be instructed to move a cursor on the screen (using a computer mouse or trackpad, for example) to select the discs that were originally highlighted. The number of discs to be tracked and the speed of the moving discs may be varied across trials. The task instructions, practice trials, and performance trials may take approximately 5 minutes to complete.

The stimuli may comprise white discs spanning 0.3 degrees visual angle (°) in radius, viewed against a black background and moving inside a white frame spanning 17.5°×17.5°. Initial movement directions for each disc can be randomly selected from 72 possible directions between 0 to $2\pi$ (radians). Each disc may move in this direction, but may be repelled when it approaches another disc or hits a wall of the frame. The speed of the discs can be about 15°/second or about 21°/second, for example, but there may be some variability over time due to the repulsions. Subject input may be received by having the subjects move a cursor to a target, and select the target with a left mouse button click.

Subjects may be shown a white frame against a black background with either 6 or 12 white discs placed in random locations inside the frame for about 300 ms. Circles or highlights may then appear around half of the discs to indicate them as targets, for about 700 ms. The circles can disappear, and after about 100 ms, the discs may move within the frame for about 5000 ms. The discs may stop moving, and after about 100 ms, a red square may appear in the center of the display screen along with a prompt instructing the subject to choose the targets (3 or 6, depending on the number of discs) by moving the red square over the targets. Subjects can control the location of the red square with a computer mouse or trackpad, and select the discs believed to be targets using a left mouse button click. A disc may turn blue when selected. Once the required number of discs is selected, white circles may appear around the true targets to provide subjects with feedback on their accuracy, for about 500 ms. Subsequently, all stimuli may offset, and subjects may be shown a blank display screen for about 200 ms before the next trial begins. Subjects may first complete a practice block of 4 trials, followed by a total of 16 performance trials.

Key dependent measures for the motion object tracking task may comprise an estimate of the number of objects that the subject can track over time ("Capacity"). Capacity can be calculated for each trial with a correction for guessing, using the following formula by developed by Hulleman (2005; see also Wolfe, Place & Horowitz, 2007):

$$K=(nc-t2)/(n+c-2t)$$

where K=capacity, n=number of total discs, c=number of target correctly identified and t=number of targets in the trial. Values of K that are less than zero, indicating pure guessing, can be reset to equal zero. The values of K may then be averaged for each condition (set size×speed).

Dynamic Motion Detection

In fast-paced, dynamic visual environments, reactions to moving targets can depend on how accurately the individual can detect the direction of motion. Individuals can differ in their sensitivity for detecting motion. The dynamic motion detection task as described herein can measure motion perception sensitivity.

Figure 7:
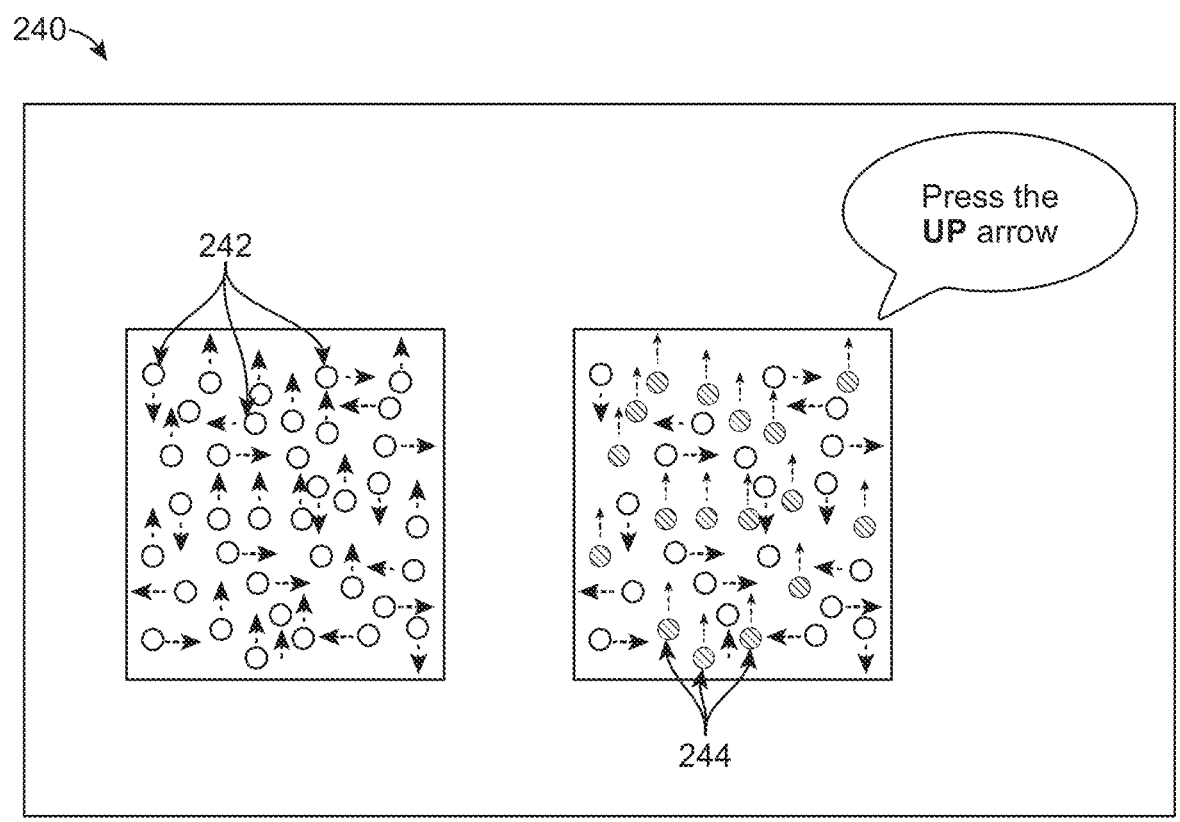
FIG. 7 shows an exemplary screenshot of a dynamic motion detection task, in accordance with embodiments.

FIG. 7 shows an exemplary screenshot of a dynamic motion detection task 240 for evaluating the ability to detect motion. Subjects may be presented with stimuli comprising randomly moving dots 242. In each trial, a specific proportion of dots 244 may be moving in the same direction rather than randomly. The ability to detect this coherent motion with a smaller proportion of coherently moving dots can indicate superior motion detection. The task instructions, practice trials, and performance trials may take approximately 3-4 minutes to complete.

The primary stimuli may comprise about 200 dots, each about 0.07 degrees visual angle (°) in radius, moving inside a square area spanning about 10°×10°. On each trial, a small portion of these dots may move in the same direction, while the remaining dots may move in random directions. The direction of each dot can be randomly drawn from 72 possible directions between 0 to 2π (radians). Subjects may provide input using their right and left hand index fingers pressing the outside buttons of a response pad.

At the beginning of a trial, subjects may be shown a centrally positioned disc, spanning 0.25° in radius, for about 500 ms. An array of about 200 moving dots may be shown subsequently, for approximately 166 ms. In each trial, a specific percentage of the dots may move in the same direction, either to the left, right, up, or down. Subjects may use the arrow keys of a keyboard to indicate the direction of coherent motion. Initially, about 37% of the dots may move in the same direction. This value may be dynamically adjusted according to the QUEST threshold procedure as known in the art (Watson & Pelli, 1983), using the response accuracy to determine the direction of the adjustment (increase the percentage for an inaccurate response, decrease the percentage for an accurate response). Subjects may complete a practice block of 6 trials, followed by a total of 40 performance trials.

Key dependent measures for the dynamic motion detection task may comprise the mean threshold estimate returned by the QUEST thresholding procedure ("Threshold"). Lower values of the Threshold generally indicate better motion detection.

Trajectory Estimation

In fast-paced, dynamic visual environments, anticipating events often relies on the ability to estimate the speed and trajectory of moving targets in space. This judgment can be especially important when a moving object is occluded during its trajectory. The trajectory estimation task described herein can measure individual differences in the ability to integrate brief exposure to a moving target's speed and trajectory to estimate its movement across occluded space.

Figure 8:
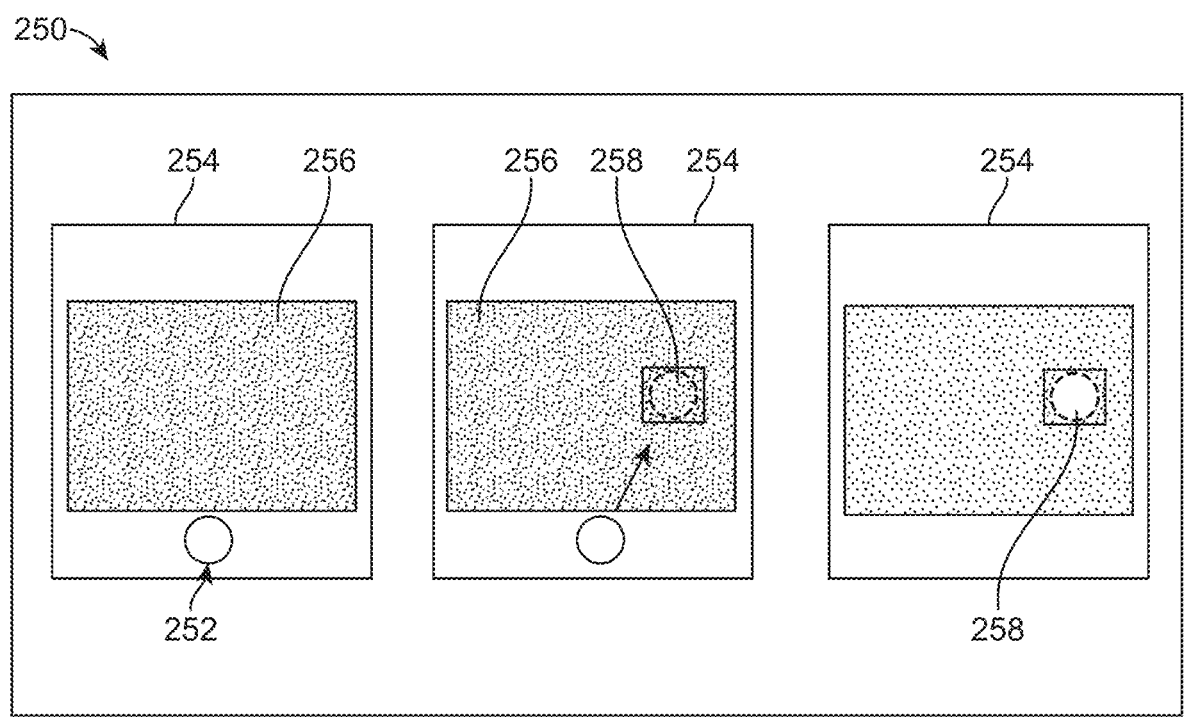
FIG. 8 shows an exemplary screenshot of a trajectory estimation task, in accordance with embodiments.

FIG. 8 shows an exemplary screenshot of a trajectory estimation task 250 for evaluating the ability to estimate a moving target's speed and trajectory. Subjects may be presented with stimuli comprising a small disc 252 at the bottom of a large frame 254 on the display. The disc may move briefly at a particular speed and at a particular angle, before disappearing behind a gray screen 256 that occludes the rest of the large frame. The subject may be instructed that the disc will continue to move at the same speed and angle after disappearing behind the gray screen, but will stop when the gray screen turns green. The subject may then be asked to move the computer mouse cursor to the spot 258 on the screen where the disc is estimated to have reached when the screen turned green. Thus, the subject must use the brief information about the moving disc's initial speed and angle to estimate its trajectory and stopping point in space after it disappears behind the occluded screen. In each trial, the disc can move at variable speeds and angles. The task instructions, practice trials, and performance trials may take approximately 3-4 minutes to complete.

The target stimulus may comprise a white disc spanning about 0.5° in radius. The target can move against a black background inside a white frame spanning about 20°×20°. Subjects may provide their inputs by moving a cursor of a computer mouse on the display screen, and clicking a left mouse button to indicate the judged position of the stopped disc.

Initially, subjects may be shown a disc near the bottom of the frame for about 1000 ms. The disc may then move at a randomly selected angle between ¾π and ¼π at varying speeds. The disc may remain in view for a length of about 500 ms, before disappearing behind the gray screen. After a variable amount of time, the gray screen may turn green, indicating that the disc has stopped moving. The subject can then estimate the stopping position by placing a mouse cursor on the spot of the screen where the disc is believed to have stopped and left-clicking to select the spot. After the subject provides the input, the disc may reappear for a short period of time in order to provide feedback regarding the subject's accuracy. The next trial can begin with the presentation of a new disc at the bottom of the frame. Subjects may complete a practice block of 6 trials, followed by a total of 20 performance trials.

Key dependent measures for the trajectory estimation task may comprise Accuracy. Accuracy may be defined by the distance error in x and y coordinates from the true location of the stopped disc is calculated and averaged across trials.

Target Movement Discrimination

In fast-paced, dynamic visual environments, reacting to a target often depends on the rapid, accurate detection of the target's initial movement. The target movement discrimination task as described herein can measure individual differences in the speed and skill at detecting the initial movement (e.g., direction or rotation) of a visual target.

Figure 9:
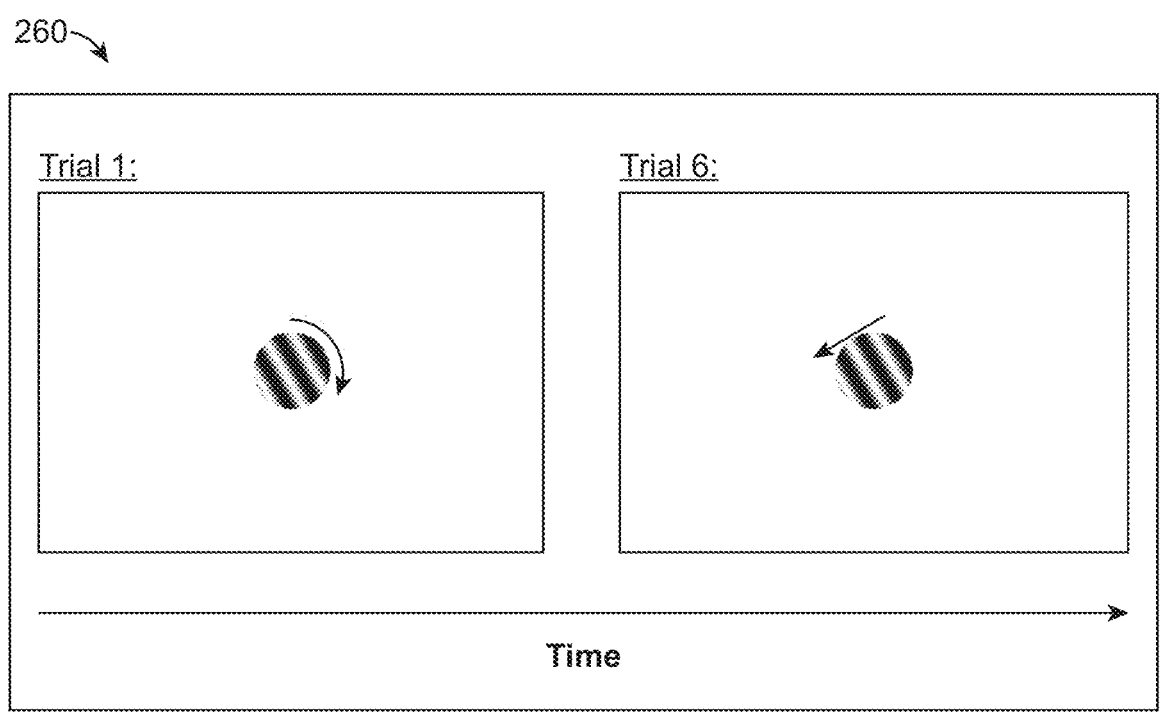
FIG. 9 shows an exemplary screenshot of a target movement discrimination task, in accordance with embodiments.

FIG. 9 shows an exemplary screenshot of a target movement discrimination task 260 for evaluating the ability to detect an initial movement of a target. A subject may be presented with a visual target that moves rotationally and/or translationally at a frequency sufficiently high to challenge the ability of human visual system to capture or discern the direction of the motion. For example, the visual target may rotate and/or translate at a frequency of at least 5 Hz, or a frequency within a range from about 5 Hz to about 30 Hz. The subject may be instructed to determine the perceived direction of motion of the visual target.

Memory and Learning

Figure 10:
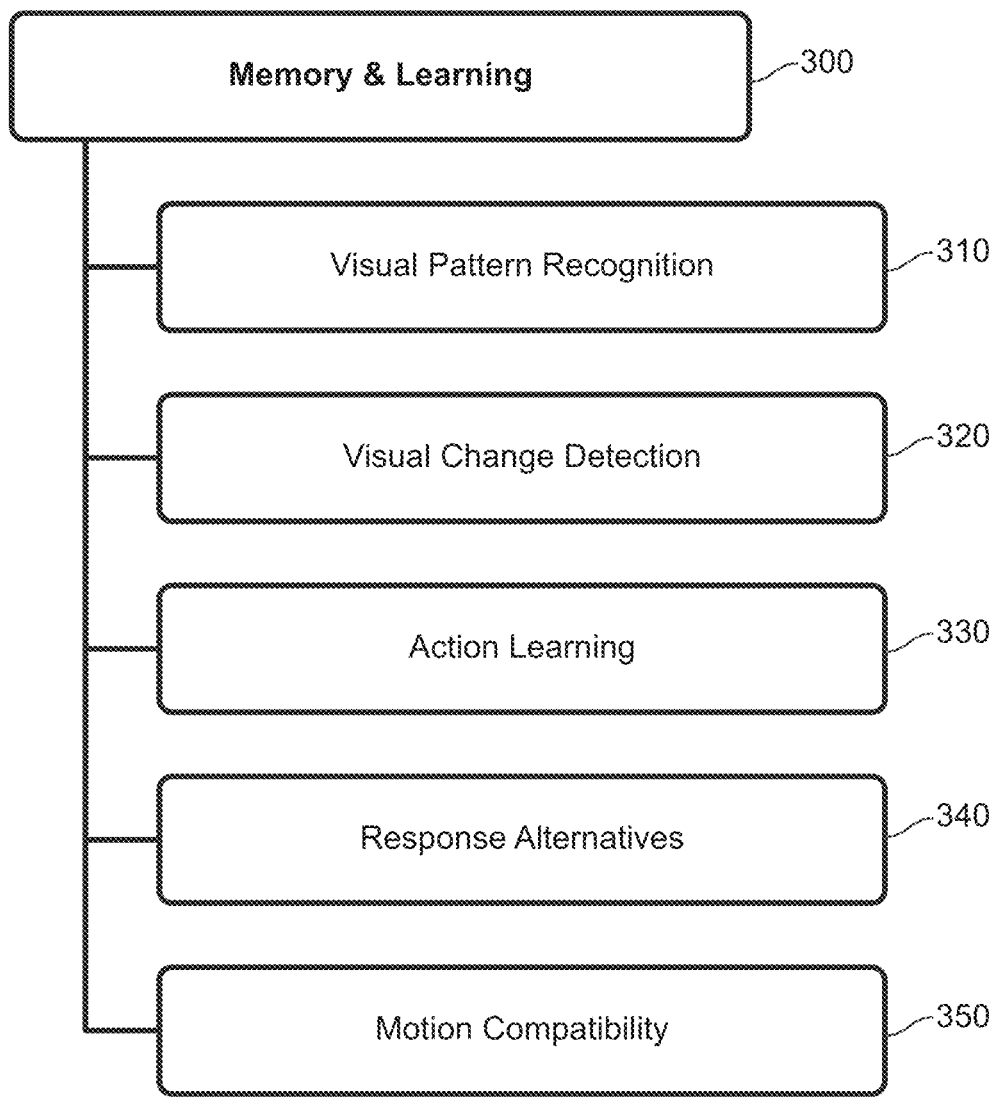
FIG. 10 shows a summary of some exemplary tasks that may be provided by the evaluation apparatus to evaluate cognitive processes related to memory and learning.

FIG. 10 shows a summary of some exemplary tasks that may be provided by the evaluation apparatus to evaluate cognitive processes related to memory and learning 300. A visual pattern recognition task 310 may measure a subject's ability to recognize and discriminate complex visual patterns. A visual change detection task 320 may measure a subject's ability to detect subtle changes in a visual scene. An action learning task 330 can measure a subject's implicit "learning on the fly", or the ability to determine how best to react in new situations. A response alternatives task 340 can measure the speed and accuracy of a subject at selecting the best response for the situation as the number of response options increases. A motion compatibility task 350 may measure a subject's speed and accuracy at translating visual motion into action based on the context. Each of these tasks can be designed and configured to test a specific set of underlying cognitive processes, by providing one or more appropriately designed stimuli and instructing the subject to provide specific input in response to the stimuli. The one or more appropriately designed stimuli may comprise, for example, stimuli designed to evaluate one or more of explicit, implicit, or procedural memory systems of the subject embodied in brain circuitries inclusive of the hippocampus, parietal cortex, mesial temporal lobes, frontal lobes, or basal ganglia.

Visual Pattern Recognition

Recognizing visual patterns is an important skill for performing in many fast-paced, visually dynamic environments. Individuals can differ in their ability to recognize and discriminate familiar patterns from novel visual patterns. The visual pattern recognition task as described herein can measure a subject's memory for spatial patterns.

Figure 11:
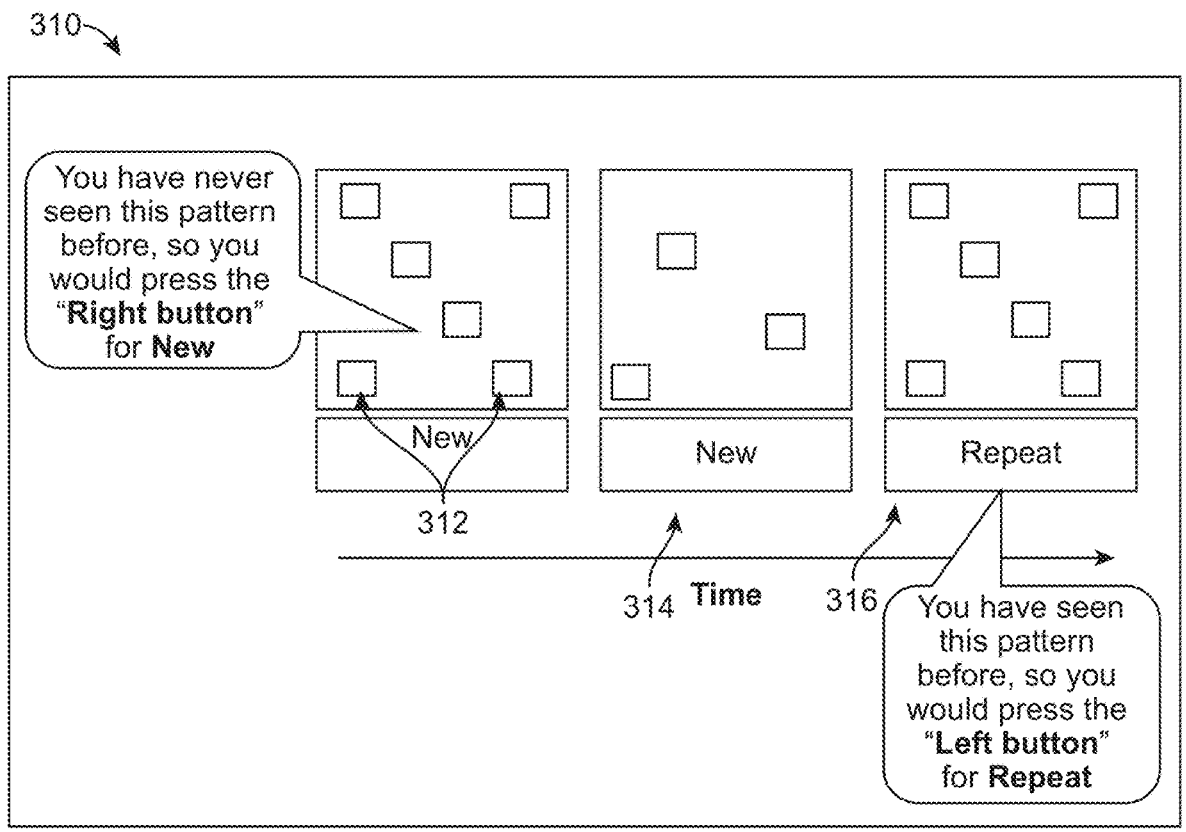
FIG. 11 shows an exemplary screenshot of a visual pattern recognition task, in accordance with embodiments.

FIG. 11 shows an exemplary screenshot of a visual pattern recognition task 310 for evaluating the ability to recognize visual patterns. Subjects may be provided with stimuli comprising a sequence of squares 312 arranged in random spatial patterns. After viewing a given pattern for about 1000 ms, subjects may be instructed to indicate whether the pattern is a "New" pattern 314 or a "Repeat" pattern 316 repeated from a previous instance in the sequence. The task instructions, practice trials, and performance trials may take approximately 3 minutes to complete.

The primary stimuli may comprise squares, spanning about 1.0×1.0 degrees visual angle (°) across, arranged in different spatial patterns. The patterns may be generated by placing 3, 6, or 12 squares on randomly selected positions of a 2×2, 3×3, or 4×4 grid, respectively. The positions may then be randomly jittered vertically and horizontally to degrade the appearance of a grid. Patterns may appear on a black background inside a white frame spanning about 15°×15°. Subjects may provide input using their right and left hand index fingers, pressing the right outside buttons of a response pad for "New" patterns, and the left outside button for "Repeat" patterns.

Initially, subjects may be shown a white frame against a black background for about 500 ms. Subsequently, a spatial pattern may appear for about 1000 ms, then offset. Subjects may be instructed to provide input indicating whether the pattern is "New" or "Repeat", during the time the pattern is visible and for about 5000 ms afterwards. The white frame may then offset, followed by a 500 ms pause before the next trial begins. The number of squares comprising the patterns can vary between 3, 6, and 12 in equal proportions. One third of the spatial patterns may be repeated four times over the course of the task, while the remaining patterns may all be unique. Subjects may view 36 patterns in total. Subjects may complete a practice block of 8 trials, followed by a total of 36 performance trials.

Key dependent measures for the visual pattern recognition task may comprise Memory (Pr), Learning Speed, and # of Trials for Learning. Memory may be defined as the difference between the proportion of repeated patterns correctly reported as "Repeat" patterns (Hits) and the proportion of new patterns incorrectly reported as "Repeat" patterns (False Alarms). Learning Speed may be defined as the difference between the response time (RT) for last correctly reported "Repeat" pattern in a trial and the response time for the first correctly reported "Repeat" pattern in a trial. # of Trials for Learning may be defined as the number of repetitions that must pass before a memory target is detected ("learned").

Rapid Spatial Memory/Visual Change Detection

An important component of performing in fast-paced, dynamic visual environments is the skill at detecting changes in the visual environment over time, and more particularly, knowing where visual targets are located in the environment and maintaining those locations in mind when attention is briefly diverted elsewhere. This skill often requires working memory for recent visual environments and the rapid comparison of those representations with the current visual environment. More particularly, perceiving and storing target locations in the working memory involves the capacity to encode locations of objects in the environment very rapidly and the ability to hold these representations in working memory to guide anticipatory actions. Individuals can differ in their capacity for storing visual representations and judging changes in the current environment, or for encoding and storing visual representations in working memory. The rapid spatial memory or visual change detection task as described herein can measure a subject's skill at detecting changes in visual scenes, or at encoding and maintaining representations of target locations in the working memory.

Figure 12A:
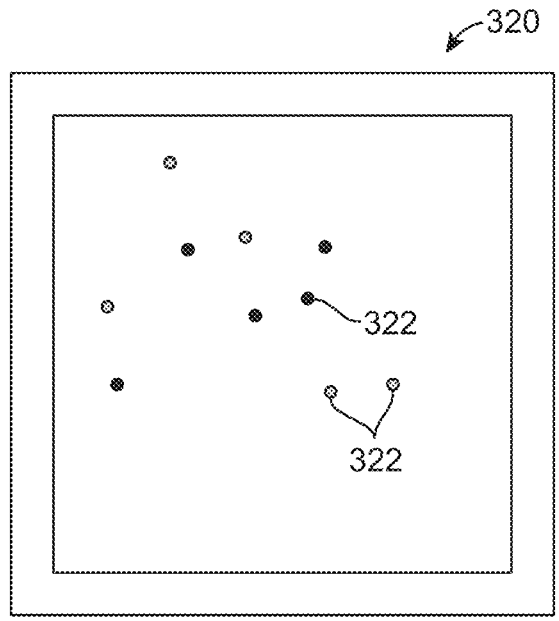
FIGS. 12A-12D show exemplary screenshots of a rapid spatial memory task or visual change detection task, in accordance with embodiments.
Figure 12B:
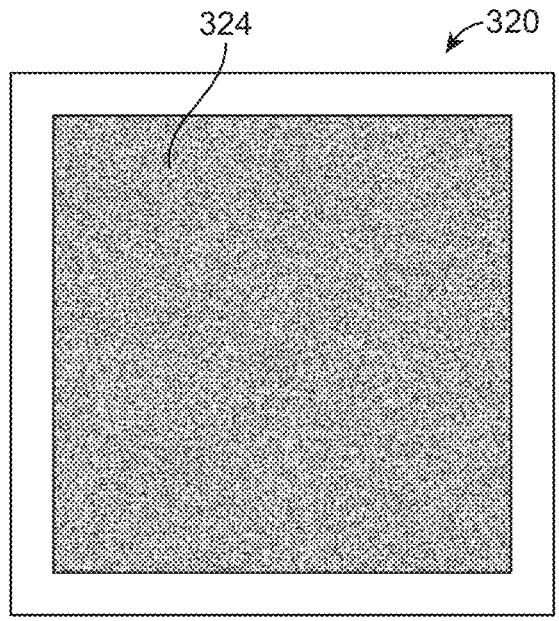
Figure 12C:
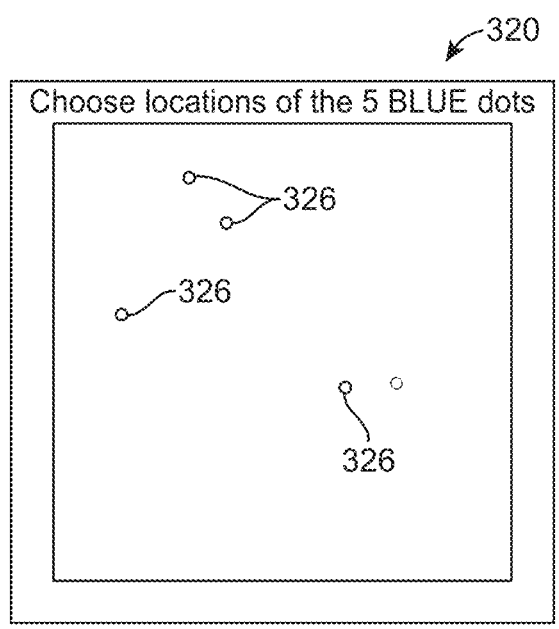
Figure 12D:
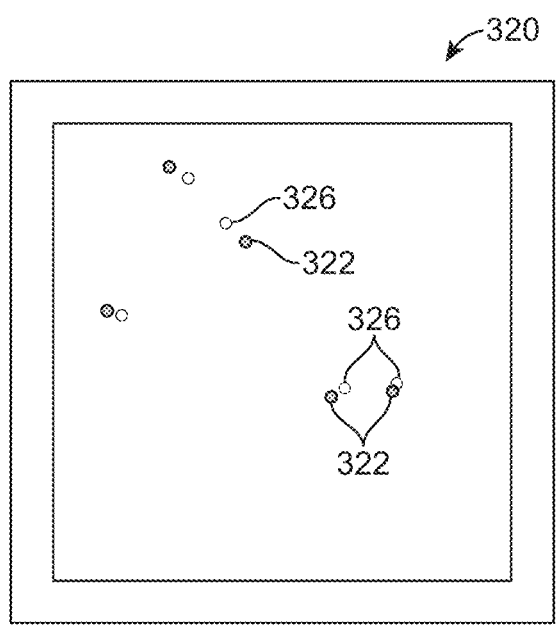

FIGS. 12A-12D show exemplary screenshots of a rapid spatial memory task 320 for evaluating the working memory of target locations in a rapidly changing environment, also referred to herein as a visual change detection task. Subjects may be provided with stimuli comprising 10 small colored discs 322 (5 blue, 5 orange) arranged in random spatial pattern on the screen, as shown in FIG. 12A. The randomly located discs may be presented briefly on the screen followed by a brief backward mask 324, as shown in FIG. 12B. After a short or long delay, subjects may then asked to indicate where either the blue or the orange discs were located on the screen by placing markers 326 at the estimated locations of the discs, as shown in FIG. 12C. After the subjects have made their selections, as shown in FIG. 12D, the targeted discs may appear in their original locations along with the markers indicated by the subject for about 1000 ms, so that the subject can gauge the accuracy of his/her selections. The task instructions, practice trials, and performance trials may take approximately 6 minutes to complete.

The primary stimuli may comprise discs, for example spanning about 0.5×0.5 degrees visual angle (°) across, arranged in random spatial patterns. Half of the 10 discs may be blue in color, and the other half may be orange. The spatial patterns of discs may appear against a gray background inside a white frame spanning about 20°×20°, for example. The spatial patterns may be backward masked by a white noise pattern created with 1×1 black and white pixels. The subject may then view a response screen displaying the phrase "Where were the 5 blue discs located?" or "Where were the 5 orange discs located?" above a blank frame. Subjects may respond by positioning the mouse cursor over a point on the screen and clicking the left button of the computer mouse.

Initially, subjects may be shown a white frame against a gray background for about 1000 milliseconds (ms). Next, a random pattern of 10 discs may appear for durations of either about 150 ms or about 1000 ms, followed immediately by a backward mask presented for about 100 ms. After a delay of about 1000 ms, a white frame may appear along with a prompt instructing the subject to indicate where either the blue or the orange discs were located. Participants may then indicate the locations of these discs by using a computer mouse to move a small cursor to each of the five locations and clicking the left mouse button. The clicking action can leave a marker at each of the locations indicated by the participant. Next, the targeted discs may appear in their original locations along with the markers indicated by the subject for about 1000 ms, so that the subject can gauge the accuracy of his/her selections. Subjects may first complete a practice block of 4 trials, followed by a total of 20 performance trials, which may be equally divided among the two pattern durations and the two possible target colors.

Key dependent measures for the rapid spatial memory task may comprise Compression (C), Correspondence, and Local Spatial Error. Compression may provide a measure of global distortions in spatial memory, and may be defined by the following equation:

$$C = \left(\frac{\sum_{i=1}^{n_r} R_i}{n_r} - R_c\right) - \left(\frac{\sum_{i=1}^{n_t} T_i}{n_t} - T_c\right)$$

where C is the measure of compression, $n_r$ is the number of responses, $R_c$ is the centroid of all responses, $R_i$ is the distance between the $i^{th}$ response and $R_c$, $n_t$ is the number of targets, $T_c$ is the centroid of all targets, and $T_i$ is the distance between the $i^{th}$ target and $T_c$. A negative value of C may indicate that memory of the spatial array fills a smaller area than the actual stimulus, or that the memory is compressed. A positive value of C may indicate that memory of the spatial array fills a larger area than the actual stimulus, or that the memory is expanded. Centroids can be calculated using hierarchical clustering (see, for example, Leskovec J., Rajaraman A., and Ullman, J. D., Mining of massive datasets, 2014). Correspondence may provide the proportion of responses that could be successfully matched to a target stimulus. A Delaunay triangulation of the target location can be constructed and then the response locations used to "query" the triangulation to find the "nearest neighbor" for each response. Competition between two responses to a single target location may be resolved by taking the closest response. Local Spatial Error may represent the average distance between a response and its corresponding target. The Local Spatial Error may only use response that were successfully paired to a target in the Correspondence measure.

Action Learning

The ability to pick up on subtle visual cues and adjust responses appropriately can be an important component of the brain's implicit learning system. This ability to "learn on the fly" may be highly advantageous for successful adaptation in fast-paced, dynamic visual environments. The action learning task as described herein can measure individual differences in the ability to learn how to react to new visual information based on probabilistic feedback.

Figure 13:
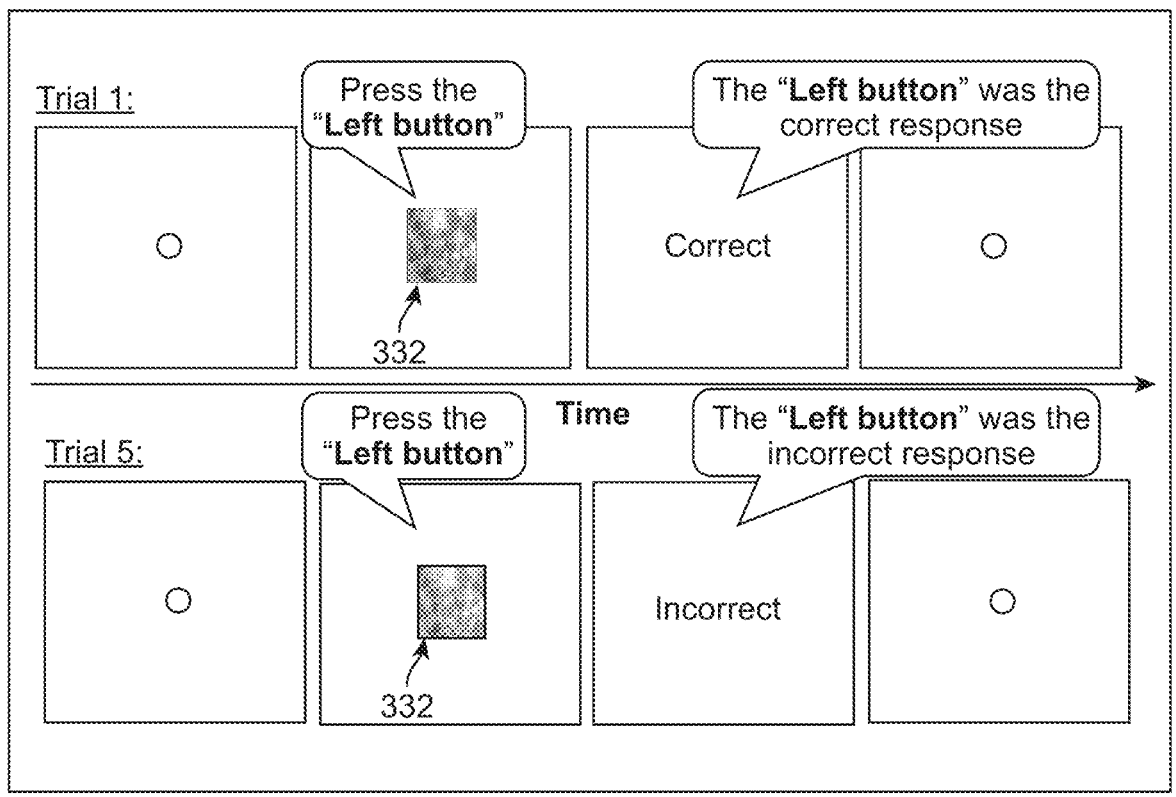
FIG. 13 shows an exemplary screenshot of an action learning task, in accordance with embodiments.

FIG. 13 shows an exemplary screenshot of an action learning task 330 for evaluating the ability to learn how to react to new visual information based on probabilistic feedback. Subjects may be presented with stimuli comprising a series of visual designs 332, one at a time, in the center of the display screen. Three unique designs may be repeated multiple times, randomly, and with equal probability. When each design appears, subjects may be instructed to make either a left hand or a right hand button press, then given immediate feedback stating that their button choice was "Correct" or "Incorrect." Subjects may be instructed that the goal of the task is to figure out for each unique design which hand is the best choice that produces the most "Correct" outcomes. Initial decisions may comprise trial-and-error, but subjects are generally expected to learn with repeated trials which hand is mapped to a "Correct" outcome for each design. Unbeknownst to the subject, each of the three designs may be associated with a different set of probabilities for receiving "Correct" or "Incorrect" feedback for each hand. For example, for a first design, choosing one hand can lead to 90% "Correct" feedback but 10% "Incorrect" feedback; conversely, choosing the other hand for this design can lead to 90% "Incorrect" feedback but 10% "Correct" feedback. For a second design, the probabilities may be adjusted to 80% and 20%, which often makes learning more difficult. For a third design, the probabilities may be adjusted to 70% and 30%, which may represent the most difficult learning condition. The task can thus measure individual differences in the ability to learn stimulus-action associations when feedback is probabilistic (as opposed to deterministic). The task instructions, practice trials, and performance trials may take approximately 4 minutes to complete.

The stimuli may comprise (1) a central fixation dot measuring about 2 mm in diameter, the dot configured to remain on the screen for about 500 ms; (2) three unique multi-colored square-shaped designs measuring about 3.3 cm in height and about 3.5 cm in width, presented for about 300 ms; and (3) feedback consisting of the words "Correct" or Incorrect" that measure about 0.5 cm in height and about 3.5 cm in width, presented at fixation for about 300 ms. Subjects may provide their input using their right and left hand index fingers to press the right or left outside buttons of a response pad.

The task may begin with the presentation of the central fixation dot that remains on the screen for about 500 ms. A trial can commence with the presentation of one of the three designs. A design may appear for about 300 ms and then disappear. From the onset of the design's appearance, the subject may be allotted about 1300 ms to provide a button press response. After a button press or after about 1300 ms have elapsed, feedback to the subject may be presented for about 300 ms. Subjects may complete a practice block of 12 trials, followed by a total of 75 performance trials. The 75 trials can represent equal numbers of each design (25 trials for each), which may be sampled randomly across the block of performance trials.

Key dependent measures for the implicit action learning task may comprise Accuracy (%) and Reaction Time (ms). Accuracy may be defined by the percent correct responses calculated separately and combined across the three designs (i.e., the 3 unique probabilities). Reaction Time may be defined as the mean time for the subject to respond (from the onset of stimulus to button press), separately and combined across the three designs.

Stimulus-Response Alternatives

The speed of performance (and often the accuracy) can suffer as the set of potential response options to choose from increases in number (e.g., choosing between two versus six possible response options). These delays can be detrimental in fast-paced, visually dynamic environments, and some individuals' performances may suffer dramatically if given too many response options to consider in a speeded decision-making context. The response alternatives task as described herein can measure individual differences in the costs to reaction speed and accuracy as response choices are made from different sized sets of response options.

Figure 14A:
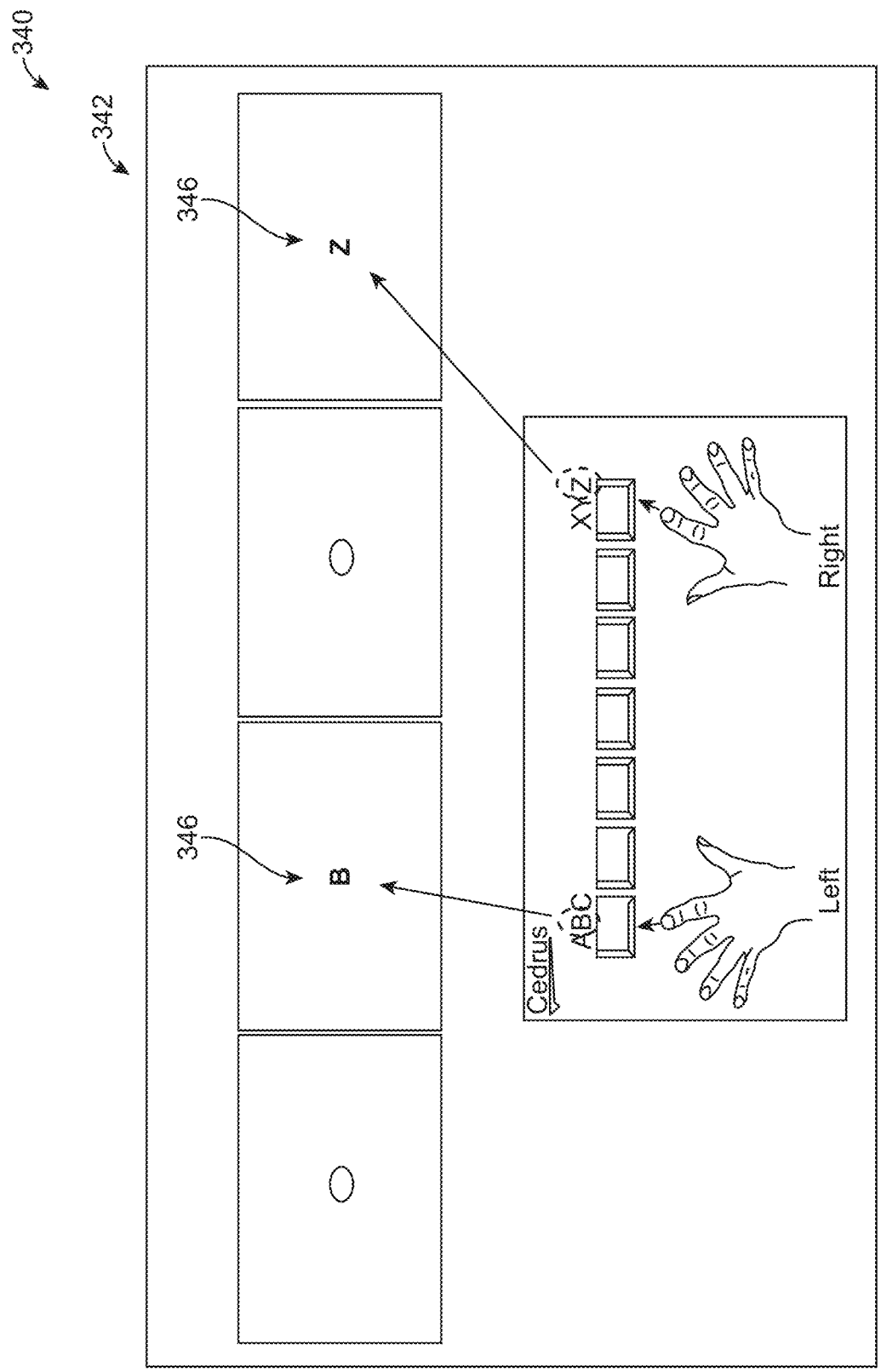
FIGS. 14A and 14B show exemplary screenshots of a response alternatives task, in accordance with embodiments.
Figure 14B:
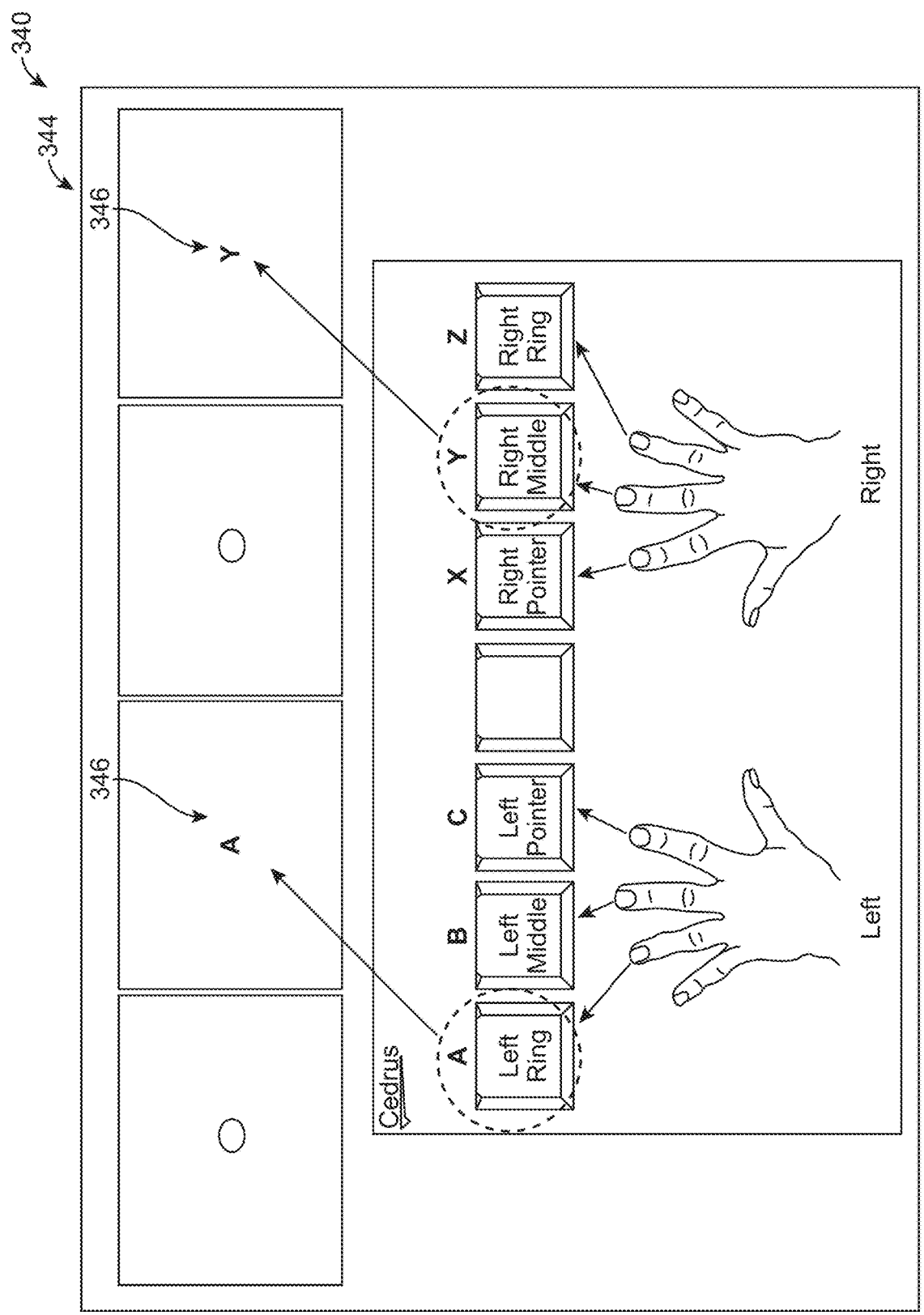

FIGS. 14A and 14B show exemplary screenshots of a response alternatives task 340 for evaluating reaction speed and accuracy with an increasing number of response options. This task may comprise two parts. On each part, subjects may be instructed to provide a speeded button press to the presentation of a letter 346. A series of letters may be presented, one at a time, in the center of the display screen. The letters may be drawn randomly and equiprobably from the set (A, B, C, X, Y, Z). FIG. 14A illustrates the first part 342 of the response alternatives task 340, comprising the 2-response alternatives portion of the task. In this part, the subject may be instructed to respond to the letters A, B, or C by pressing an outside left button of a response pad with the left hand index finger, and to respond to the letters X, Y, or Z by pressing an outside right button of the response pad with the right hand index finger. In this scenario, even though there are six possible letter stimuli, there are only two possible response options for each hand (3 letters mapped to each hand). In second part 344, shown in FIG. 14B, the 6-response alternatives portion of the task, six letters may be presented to the subject as in the first part, but each letter may be mapped to a different finger. For example, the letters A, B, and C may still be mapped to the left hand but require responses with the left ring, middle, and index fingers, respectively. Similarly, the letters X, Y, and Z may still be mapped to the right hand, but to the right index, middle, and ring fingers, respectively. The task can measure individual differences in the reaction time and accuracy costs when the number of possible response options increases from 2 to 6. The task instructions, practice trials, and performance trials may take approximately 5 minutes to complete.

The stimuli may comprise (1) a central fixation dot measuring about 0.2 cm diameter that appears for about 250 ms, and (2) the letters A, B, C, X, Y, and Z, measuring about 0.8 cm in height and about 0.5 cm in width. Subjects may provide input by pressing buttons of a response pad.

The task may begin with the presentation of the fixation dot for a duration of about 250 ms. A trial may commence with the random but equiprobable presentation of one of six letter stimuli. Each letter may appear for about 200 ms and then disappear. From the onset of the letter presentation, the subject may be given about 1000 ms to provide an input as instructed. For each part (2 vs. 6 response alternatives), subjects may first complete a practice block of 12 trials, followed by a total of 36 performance trials. The 36 trials can represent equal numbers of each letter, occurring randomly across the block of trials.

Key dependent measures for the response alternatives task may comprise Accuracy (%), Reaction Time (ms), and Response Alternative Costs. Accuracy may be defined by the percent correct responses calculated separately for 2- and 6-response alternatives conditions. Reaction Time may be defined as the mean time for the subject to respond (onset of stimulus to button press) on correct reactions, separately for 2- and 6-response alternatives conditions. Response Alternative Costs may be defined as the difference in mean accuracy rates and reaction times between 2- and 6-response alternatives conditions.

Motion Compatibility

In fast-paced, dynamic visual environments, individuals often need to quickly and accurately translate observed motion of a visual target into a specific response choice. Depending on the context, the motion of a visual target may lead to the decision to choose completely different responses. Moreover, an individual may sometimes need to determine the processing of the context as the target is moving. Individuals can vary not only in speed and accuracy of their ability to translate a moving visual target into an action decision, but also in the speed with which they can process contextual cues to guide their decisions. The motion compatibility task described herein can measure individual differences in the speed and accuracy of translating the motion of a visual target into distinct response choices based on contextual cues.

Figure 15:
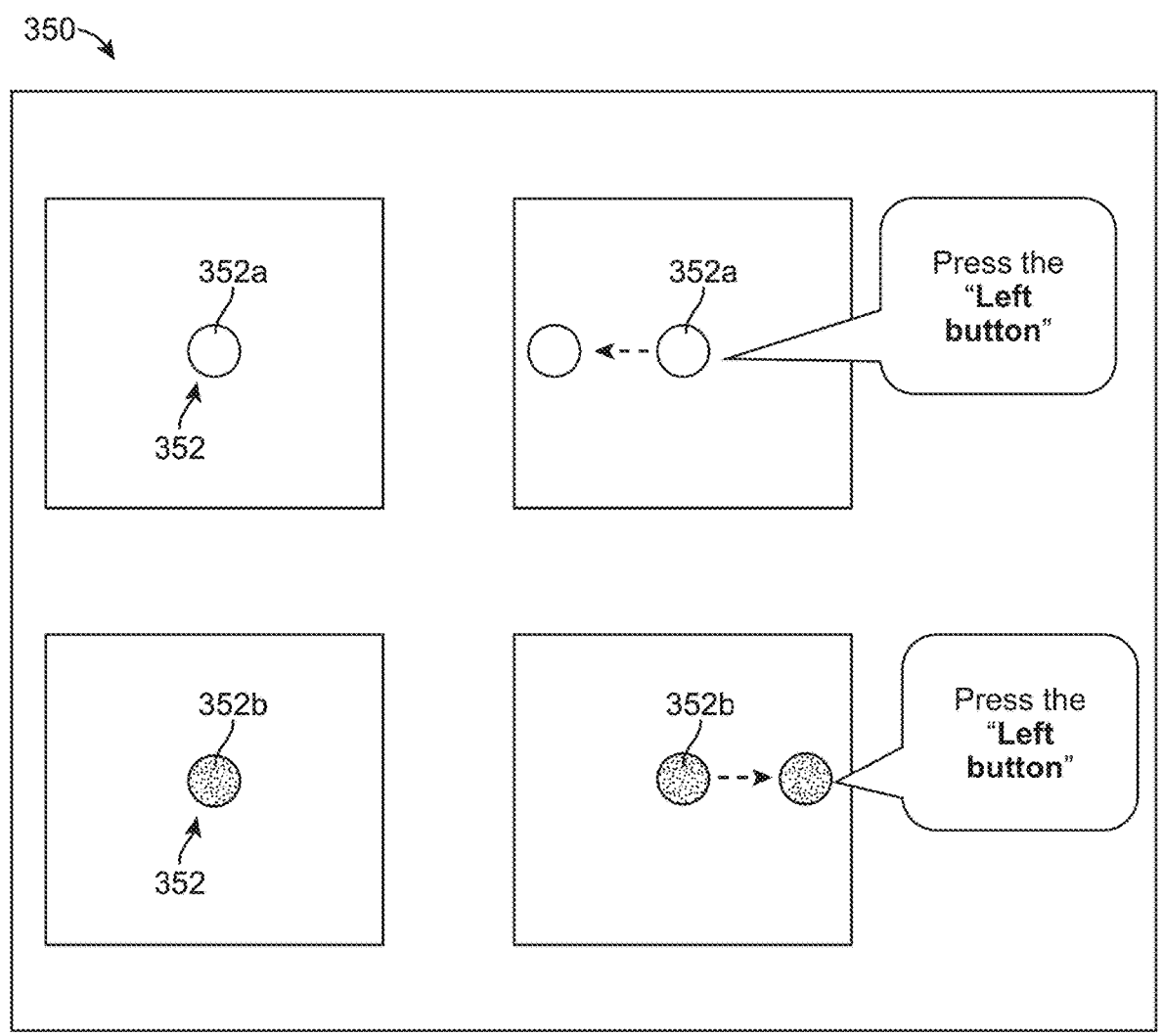
FIG. 15 shows an exemplary screenshot of a motion compatibility task, in accordance with embodiments.

FIG. 15 shows an exemplary screenshot of a motion compatibility task 350 for evaluating the speed and accuracy of translation the motion of a visual target into distinct response choices. Subjects may be provided with stimuli comprising a series of balls 352, presented one at a time and appearing in the center of the display screen. A ball may move rapidly to the left or to the right. Balls appear in with equal probability in one of two colors, for example either in bluish-green 352a or in purple 352b. If the ball appears in bluish-green, then the subject may be instructed to respond with the hand that is in the same (i.e., compatible) direction as the moving ball (e.g., if the ball moves left, make a left hand button press). If the ball appears in purple, the subject may be asked to respond with the hand that is in the opposite direction (i.e., incompatible) of the moving ball (e.g., if the ball moves left, make a right hand button press). An additional factor may be manipulated in this task. After a ball appears on the screen, its lateral movement may begin after a 50 ms delay (generally perceived as immediately), or after a 500 ms delay. The 500 ms delay can generally provide sufficient time for a subject to preload the stimulus-response translation rule prior to the initiation of the ball's movement. In contrast, in the 50 ms delay condition, the subject needs to process the translation rule in parallel with the processing of the ball's movement. This manipulation can produce two key effects of interest: (1) when given sufficient time to preload the stimulus-response translation rule (500 ms condition), performance may measure individual differences in typical compatibility effects, whereby reactions are slower and less accurate for incompatible compared to compatible trials; and (2) when not provided sufficient time to preload the stimulus-response translation rule (50 ms condition), performance may measure individual differences in the speed of stimulus-response translation, which is computed as the reaction time slowing when subjects do not have preload time (50 ms condition) compared to when they have time to preload the translation rule (500 ms condition). The task instructions, practice trials, and performance trials may take approximately 3 minutes to complete.

The stimuli may comprise (1) a ball measuring about 0.6 cm that appears in one of two colors in the exact center location of the fixation cross, and then moves laterally to the left or to the right at a speed of about 8 cm/sec for a distance of about 4.5 cm. Subjects may provide input response by pressing the left and right outside buttons of a response pad with their right and left hand index fingers, respectively.

The task may begin with the presentation of a ball immediately in the center of the screen. The ball may remain stationary in the center of the screen for either 50 ms or 500 ms, before moving in either the left or right direction. The subject may be given about 1550 ms (measured from the onset of the ball's initial movement) to respond with a left or right button press on the response pad. The determination of which button to press is based on a pre-determined mapping rule established by the ball's color, which is provided to the subject. If a ball appears in the color green, the subject is instructed to respond with the hand that is in the same direction as the ball's move (e.g., right hand button press to a ball that moves to the right); if a ball appears in purple, the subject is instructed to respond with the hand that is opposite the direction of the moving ball (e.g., left hand button press to a ball that moves to the right). After the 1550 ms time period expires, the next trial may begin. Subjects may first complete a practice block of 16 trials, followed by a total of 80 performance trials. Each combination of the ball's color (compatible, incompatible), motion direction (left, right), and movement delay (50 ms delay, 500 ms delay) may occur randomly and with equiprobability across trials.

Key dependent measures for the motion compatibility task may comprise Accuracy (%), Reaction Time (ms), Stimulus-Response Compatibility Effects, and Preload Effects. Accuracy may be defined as the percent correct responses calculated separately for compatible and incompatible trials as a function of motion delay. Reaction Time may be defined as the mean time for the subject to respond (onset of stimulus motion to button press) on correct reactions, separately for compatible and incompatible trials as a function of motion delay. Stimulus-Response Compatibility Effects may be defined as the difference in mean accuracy rates and reaction times between Compatible and Incompatible trials as a function of motion delay. Preload Effects may be defined as the difference in mean accuracy rates and reaction times between motion delays conditions (5 ms, 500 ms), collapsed across levels of Stimulus-Response Compatibility.

Command and Control

Figure 16:
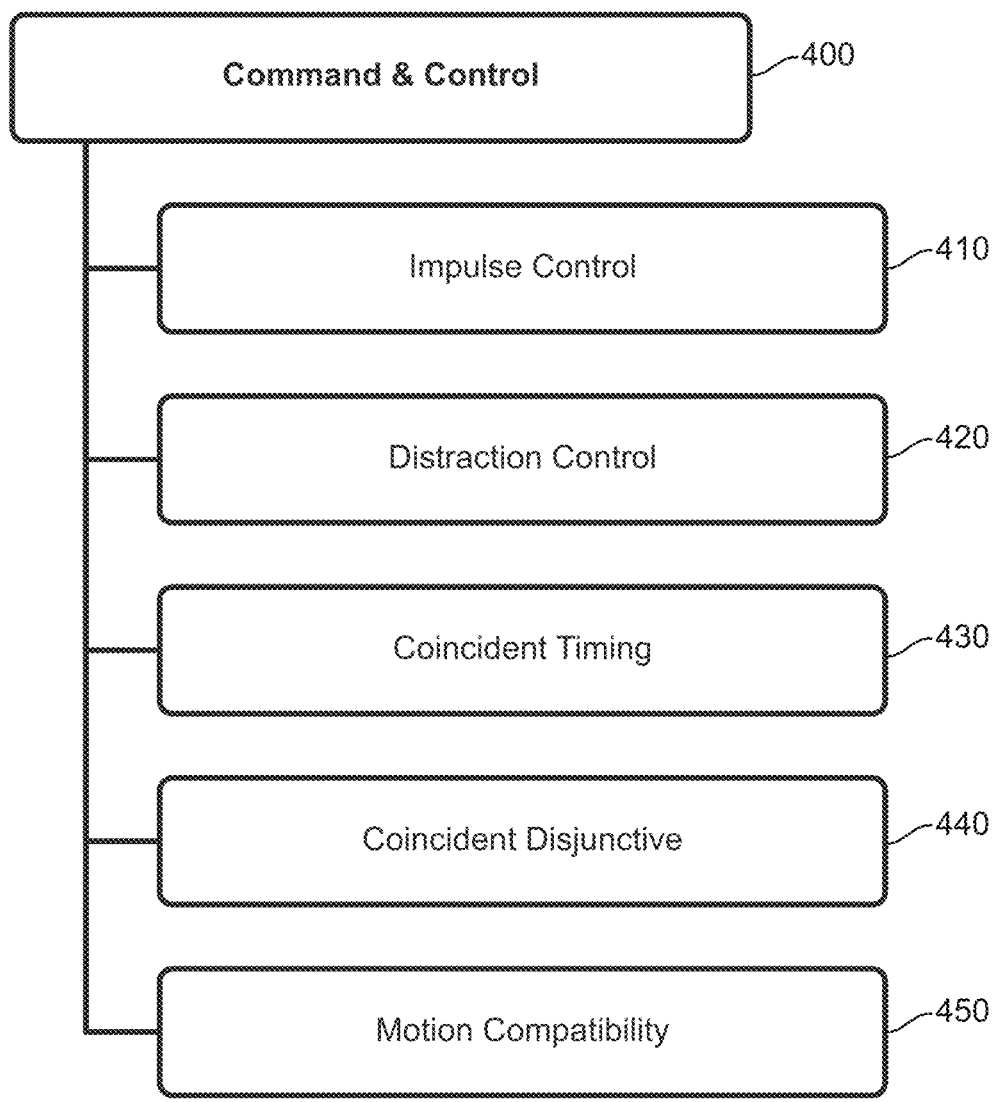
FIG. 16 shows a summary of some exemplary tasks that may be provided by the evaluation apparatus to evaluate cognitive processes related to command and control.

FIG. 16 shows a summary of some exemplary tasks that may be provided by the evaluation apparatus to evaluate cognitive processes related to command and control 400. An impulse control task 410 may measure a subject's ability to prevent and recover from initial action impulses. A distraction control task 420 may measure a subject's ability to minimize performance costs when faced with salient visual distractors. A coincident timing task 430 may measure a subject's ability to control the timing of reactions to rapidly moving visual targets. A coincident disjunctive task 440 may measure a subject's ability to regulate the decision to act or withhold action based on whether a moving visual target is predicted to intercept or avoid a point in space. A motion compatibility task 450 may measure a subject's speed and accuracy at translating visual motion into action based on the context. The motion compatibility task 450 may be the same as the motion compatibility task 350 illustrated in FIG. 15, described in relation to the evaluation of cognitive processes related to memory and learning. Each of these tasks can be designed and configured to test a specific set of underlying cognitive processes, by providing one or more appropriately designed stimuli and instructing the subject to provide specific input in response to the stimuli. The one or more appropriately designed stimuli may comprise, for example, stimuli designed to evaluate one or more of executive cognitive control systems of a subject embodied in brain circuitries inclusive of dorsolateral and ventrolateral prefrontal cortex, motor cortex, premotor cortex, pre-supplementary motor cortex, parietal cortex, cingulate cortex, or subcortical basal ganglia structures.

For some of the tasks described herein, the processor of the evaluation apparatus may comprise instructions to measure an ipsilateral response to a stimulus shown on a first side of the display, and a contra lateral response to the stimulus shown on a second side of the display, wherein the first side may be separated from the second side with a midline of the display when a midline of the subject is aligned with the midline of the display. The right stimulus may be presented on a right side of the display, and the subject may respond with a right hand to measure the ipsilateral response. The left stimulus may be presented on a left side of the display, and the subject may respond with the right hand to measure the contralateral response. A time of response of the subject, measured from the presentation of the right stimulus to the subject providing an input with the right hand, can determine the ipsilateral response. A time of response of the subject, measured from the presentation of the left stimulus to the subject providing an input with the right hand, can determine the contralateral response. Similarly, a left stimulus may be presented on a left side of the display, and the subject may respond with a left hand to measure the ipsilateral response. A right stimulus may be presented on a right side of the display, and the subject may respond with the left hand to measure the contralateral response. A time of response of the subject, measured from presentation of the left stimulus to the subject providing an input with the left hand, can determine the ipsilateral response. A time of response of the subject, measured from presentation of the right stimulus to the subject providing an input with the left hand, can determine the contralateral response.

Impulse Control

The ability to overcome impulsive motor reactions is a fundamental component of the brain's cognitive control system. In fast-paced, dynamic visual environments, spatial and directional stimulus information may trigger spontaneous response impulses that can lead to overt errors in behavior or interfere with the speed of executing a desired action. The impulse control task as described herein can measure individual differences in susceptibility to acting on these impulses and the proficiency of reducing interference from impulsive response tendencies.

Figure 17:
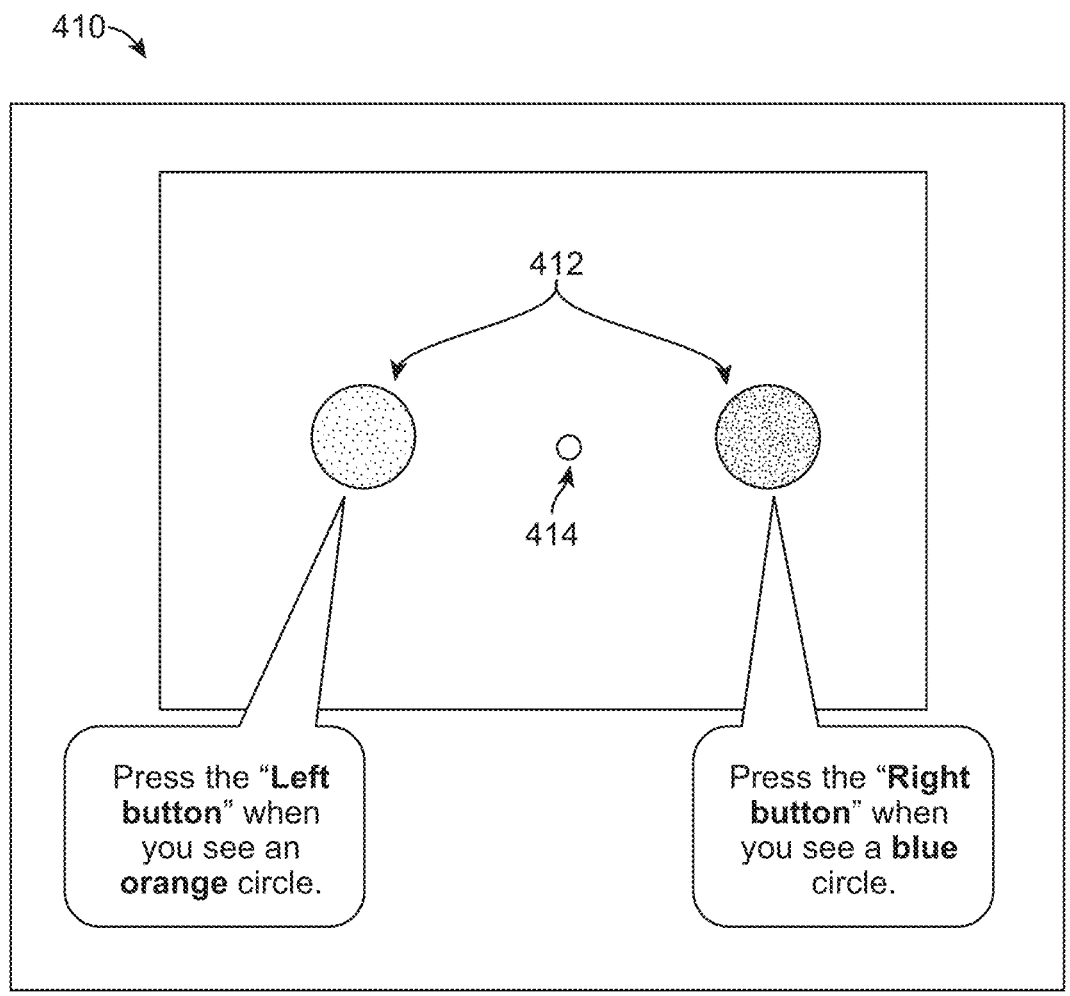
FIG. 17 shows an exemplary screenshot of an impulse control task, in accordance with embodiments.

FIG. 17 shows an exemplary screenshot of an impulse control task 410 for evaluating impulse control. Subjects may be provided with stimuli comprising a series of colored circles 412, wherein each circle appears either to the left or to the right of a central fixation point 414. Subjects may be instructed to provide a speeded left or right hand button press to a response pad, based on the color of a presented circle (e.g., orange=left press; blue=right press). When the circle color calls for a response with the hand that is on the same side of visual space as the circle appears (Corresponding trials), reactions usually tend to be fast and highly accurate. When the color of the circle calls for a response with the hand that is on the opposite side of visual space as the circle appears (Non-Corresponding trials), reactions usually tend to be more error-prone (e.g., impulsive errors are made) and correct reactions tend to be slowed relative to Corresponding trials. Individuals can differ in the magnitudes of these costs. The task instructions, practice trials, and performance trials may take approximately 3 minutes to complete.

The stimuli can comprise (1) a central fixation dot measuring about 0.5 cm in diameter, which remains on the screen at all times, and (2) circles in two distinct colors of equal luminance, measuring about 1.5 cm in diameter and spaced about 2 cm from the fixation dot (center to center). The circles may be configured to flash on the screen for about 250 ms. Subjects may provide their input using their right and left hand index fingers pressing the right outside and left outside buttons, respectively, of a response pad.

The task may begin with the presentation of the fixation dot that may remain on the screen for the entire task. A trial can commence with the random but equiprobable presentation of one of the two circle colors. A circle may appear for about 250 ms and then disappear. From the onset of the circle presentation, the subject may be allotted about 1000 ms to provide an input by pressing a button on the response pad. After the allotted time has expired, the next trial may begin with the presentation of the fixation dot. Subjects may first complete a practice block of 20 trials, followed by a total of 80 performance trials. The 80 trials can represent equal numbers of each circle color presented to each visual field (i.e., 20 blue circles to the left visual field, 20 blue circles to the right visual field, 20 orange circles to the left visual field, 20 orange circles to the right visual field). The 80 trials also contain equal numbers of Corresponding and Non-Corresponding trial types, distributed equally across left and right hands. The order of trial combinations may be random.

Key dependent measures for the impulse control task may comprise Accuracy (%), Reaction Time (ms), and Simon Conflict Effects. Accuracy may be defined as the percent correct responses, calculated separately for Corresponding and Non-Corresponding trials. Reaction Time may be defined as the time for the subject to respond (onset of stimulus to button press) on correct reactions, separately for Corresponding and Non-Corresponding trials. Simon Conflict Effects may be defined by the difference in mean accuracy rates and reaction times between Corresponding and Non-Corresponding trials.

Distraction Control

The ability to control reactions in the face of distraction is a fundamental component of the brain's cognitive control system. In fast-paced, dynamic visual environments, distracting information in the visual field can interfere with the ability to respond quickly and accurately to critical target information. The distraction control task as described herein can measure individual differences in the ability to respond proficiently in the face of visual distraction.

Figure 18:
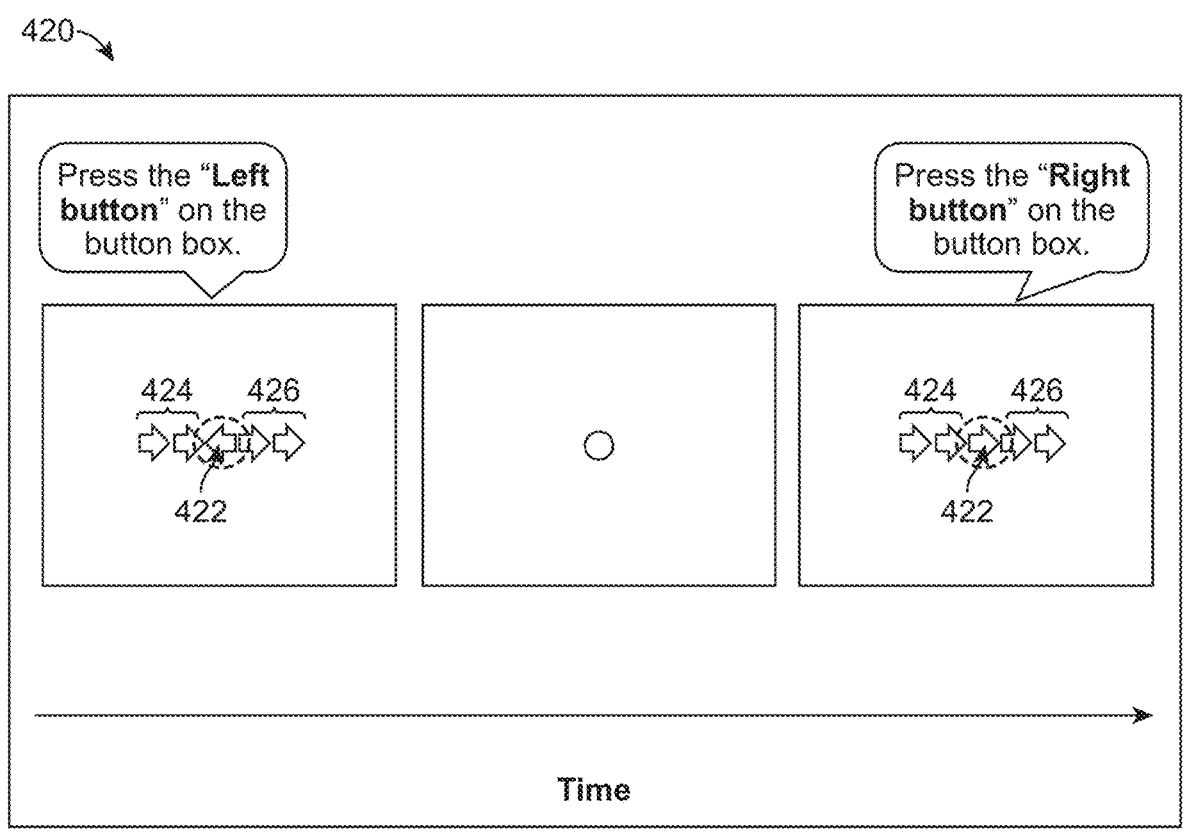
FIG. 18 shows an exemplary screenshot of a distraction control task, in accordance with embodiments.

FIG. 18 shows an exemplary screenshot of a distraction control task 420 for evaluating the ability to control distractions. Subjects may be provided with stimuli comprising a centrally located left or right pointing arrow 422, surrounded by 2 flanking arrows to its left 424 and 2 flanking arrows to its right 426 along the horizontal axis. The flanking arrows 424 and 426 may either point in the same direction as the center arrow 422 (i.e., Congruent with the target) or in the opposite direction as the center arrow (i.e., Incongruent with the target). Subjects may be instructed to provide input using their left or right hands to press buttons on a response pad, in the direction of a centrally located left or right pointing arrow (left arrow=left press; right arrow=right press). Reaction time usually tends to be slower and error rates higher when the flanking arrows are Incongruent, compared to when they are Congruent. Individuals can differ in the magnitudes of these costs. The task instructions, practice trials, and performance trials may take approximately 3 minutes to complete.

The stimuli may comprise (1) a central fixation dot measuring about 0.5 cm in diameter that appears for about 50 ms prior to the onset of the arrow array having dimensions of about 1.5 cm by about 7 cm, (2) an arrow array consisting of 5 arrows pointing to the left, (3) an arrow array consisting of 5 arrows pointing to the right, (4) an arrow array consisting of a center arrow pointing to the left and 4 flanking arrows pointing to the right, and (5) an arrow array consisting of a center arrow pointing to the right and 4 flanking arrows pointing to the left. Subjects may provide input with their right and left hand index fingers, using outside buttons on a response pad.

The task may begin with the presentation of the fixation dot. A trial may commence with the random but equiprobable presentation of one of four possible arrow arrays. An arrow array may appear for about 250 ms and then disappear. From the onset of the arrow array presentation, the subject may be allotted about 1000 ms to provide a left or a right button press response. Subjects may first complete a practice block of 16 trials, followed by a total of 80 performance trials. The 80 trials may represent 20 presentations of each of the four arrow arrays delivered in random order. Thus, the 80 trials can consist of 40 Congruent trials and 40 Incongruent trials distributed equally across left and right hands.

Key dependent measures for the distraction control task may comprise Accuracy (%), Reaction Time (ms), and Flanker Interference Effects. Accuracy may be defined as the percent correct responses, calculated separately for Congruent and Incongruent trials. Reaction Time may be defined by the mean time for the subject to respond (onset of stimulus to button press) on correct reactions, separately for Congruent and Incongruent trials. Flanker Interference Effects may be defined by the difference in mean accuracy rates and reaction times between Congruent and Incongruent trials.

Coincident Timing

Performing in dynamic visual environments often involves timing one's actions to the arrival of a moving visual target to a point in space. The more variable the speed of the moving target, the more challenging it can be to time an action to its arrival at a target location. The coincident timing task as described herein can measure individual differences in the accuracy of timing a response to the arrival of visual targets (moving at variable speeds) to a point in space.

Figure 19:
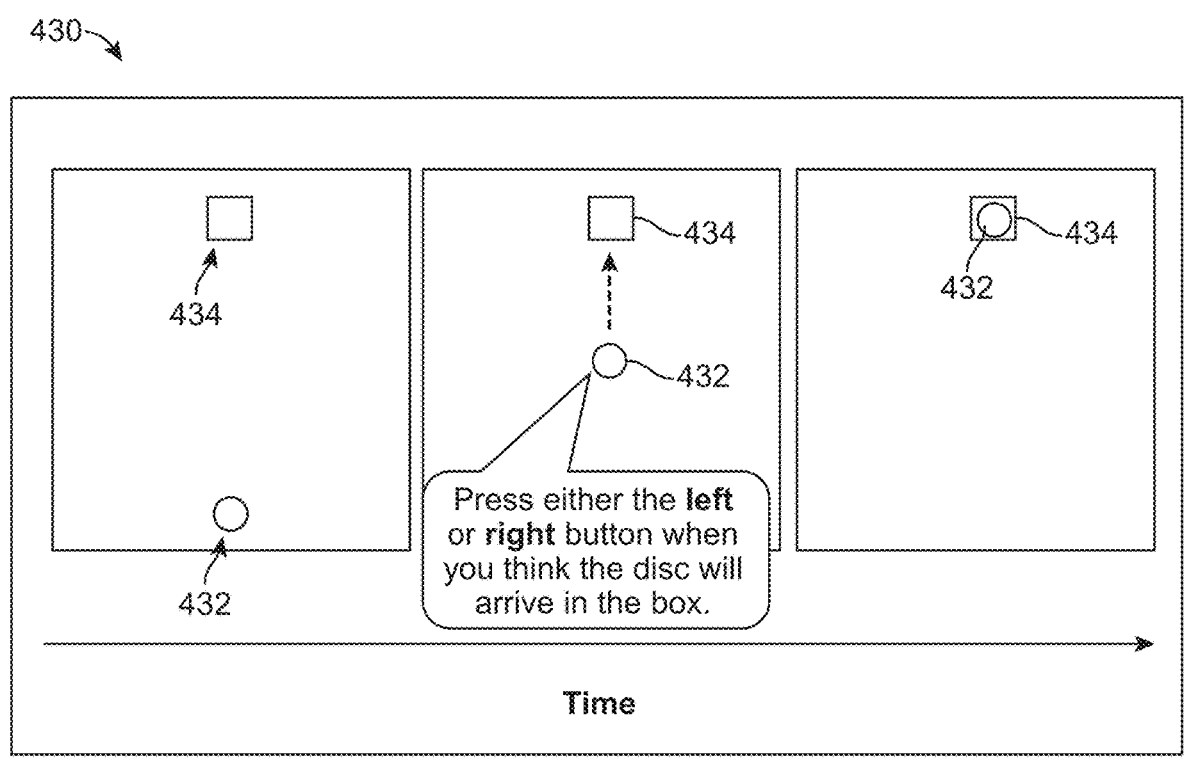
FIG. 19 shows an exemplary screenshot of a coincident timing task, in accordance with embodiments.

FIG. 19 shows an exemplary screenshot of a coincident timing task 430 for evaluating accuracy of timing a response to the arrival of visual targets to a point in space. Subjects may be presented with stimuli comprising a small circular disc 432 at the bottom the display screen and a small box 434 located at the top of the screen, directly above the small disc. For each trial, the disc may move toward the small box, and subjects may be instructed to press a single button on a response pad with their preferred hand when the disc arrives in the small box (i.e., when the disc is centered in the small box). The disc may stop moving when the subject presses the button. The disc can move unpredictably at varying speeds across trials. The task instructions, practice trials, and performance trials may take approximately 5 minutes to complete.

The stimuli may comprise white discs spanning about 0.5 degrees visual angle (°) in diameter, viewed against a black background and moving inside a white frame spanning about 20°×20°. The small box may measures about 0.9°×

0.9°. Subjects may provide input via a button press with the preferred hand on the response pad.

Initially, subjects may be shown a large white frame against a black background with a small box positioned at the top, center of the frame. A disc may then appear, about 14° below the small box. After a variable length of time ranging from about 500 to about 1000 ms, the disc may move towards the small box at a speed of, for example, 28.17, 29.87, 31.56, or 33.26°/second. The speed can vary randomly and with equiprobability across trials. The trial may end when the subject presses the button to stop the disc, or when the disc has passed through the box and traveled to the top of the frame. An inter-trial interval of about 1000 ms may transpire before the start of the next trial, which can begin with the presentation of another disc. Subjects may complete a practice block of 4 trials, followed by a total of 24 performance trials.

Key dependent measures for the coincident timing task may comprise Accuracy, defined by the estimated accuracy of stopped discs computed as a distance error from center of stopped disc to center of box in x and y coordinates.

Coincident Disjunctive Task

Performing in dynamic visual environments may require quick decisions about whether to react or to withhold a reaction based on the predicted intersection of a moving target and a point in space. Making such decisions can require the rapid integration of a moving target's speed and trajectory, in order to predict whether the moving target will intercept or avoid a target along its trajectory. The coincident disjunctive task as described herein can measure individual differences in the accuracy and speed of deciding whether a moving target will intercept or miss a target location along its trajectory.

Figure 20:
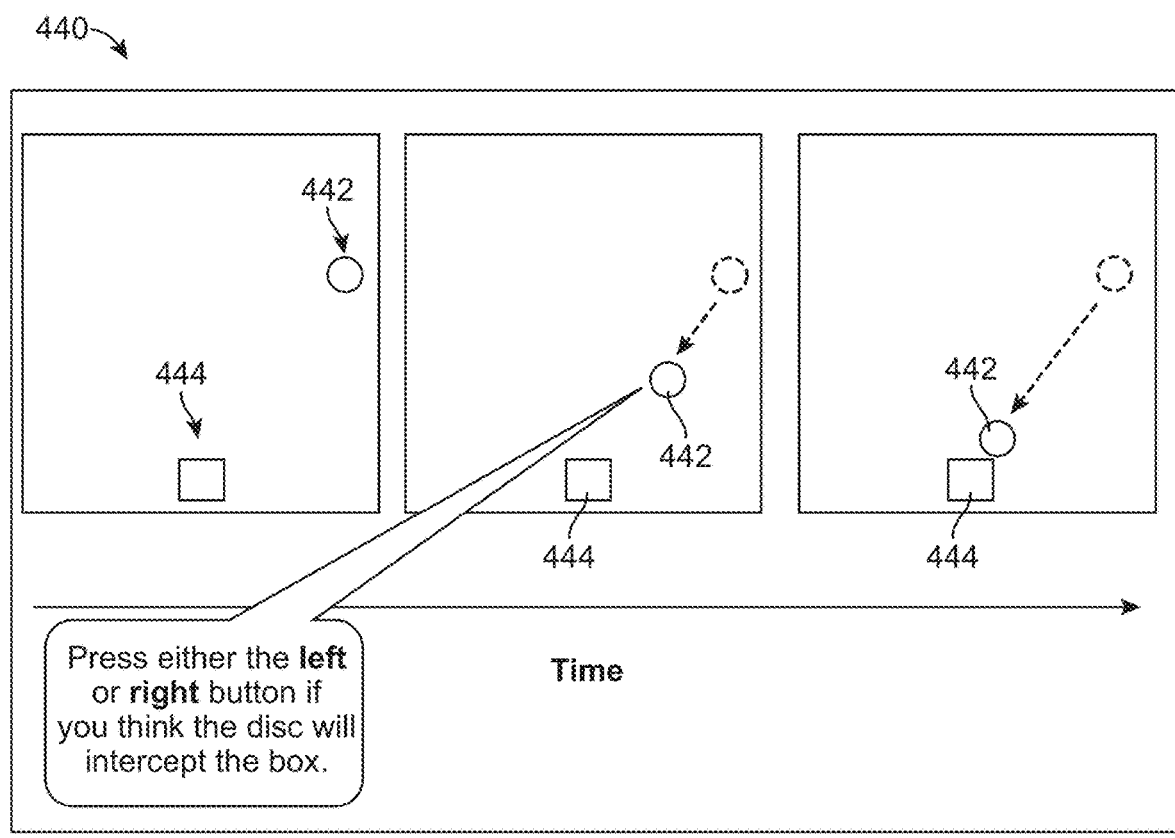
FIG. 20 shows an exemplary screenshot of a coincident disjunctive task, in accordance with embodiments.

FIG. 20 shows an exemplary screenshot of a coincident disjunctive task 440 for evaluating the accuracy and speed of deciding whether a moving target will intercept or miss a target location along its trajectory. Subjects may be presented with stimuli comprising a small circular disc 442 appearing at one of several locations across the top of a large window frame. A small square box 444 may also be presented at the bottom of the frame. The disc may appear and move toward the box. Subjects may be instructed to press a button on a response pad using a preferred hand, as soon as they judge that the disc will intercept the small box; conversely, subjects may be instructed to withhold a response if they judge that the disc will not intercept the box. If a subject presses a button, the disc can change color immediately but continue on its course, so that the subject can see whether the disc actually intersects the box. The task instructions, practice trials, and performance trials may take approximately 5 minutes to complete.

The stimuli may comprise white discs spanning about 0.5 degrees visual angle (°) in diameter, viewed against a black background and moving inside a white frame spanning about 20°×20°. The small box may measures about 0.9°× 0.9°. Subjects may provide input via a button press with the preferred hand on a response pad.

Initially, subjects may be shown a large white frame against a black background with a small box positioned at the bottom, center of the frame. A disc can appear at the top of the screen for a variable duration of time, ranging from about 500 ms to about 1000 ms, and then move at a speed of, for example, 28.17, 29.87, 31.56, or 33.26°/second toward the box. The disc may have a 50% probability of intersecting the box, and the difficulty of the judgment can vary based on where the disc intersects the box (e.g., intersects the middle of the box versus the edges of the box) or how closely it misses the box (e.g., misses wide or misses by a narrow margin). The trial may end after the disc passes through or beside the box and reaches the frame. An inter-trial interval of about 1000 ms may then transpire before the start of the next trial, which can begin with the presentation of another disc. Subjects may first complete a practice block of 4 trials, followed by a total of 24 performance trials.

Key dependent measures for the coincident disjunctive task may comprise Accuracy (%) and Decision Speed (ms). Accuracy may be defined by the sum of the number of correct responses made to discs that intersect the box and the number of correct withholdings of responses to discs that do not intersect the box, divided by the total number of discs. Decision Speed may be defined by the average reaction time of button presses for correct decisions that the disc was expected to intersect the box.

Additional Exemplary Tasks

Stop-Signal Task

A stop-signal task may comprise another exemplary task that may be provided by the evaluation apparatus to evaluate cognitive processes related to visual perception. Performing in reaction-oriented, dynamic environments often requires sudden stopping or inhibition of ongoing action. The stop-signal task as described herein can be used to quantify both the speed of initiating action and the speed of inhibiting action to visual cues in the environment.

Figure 21:
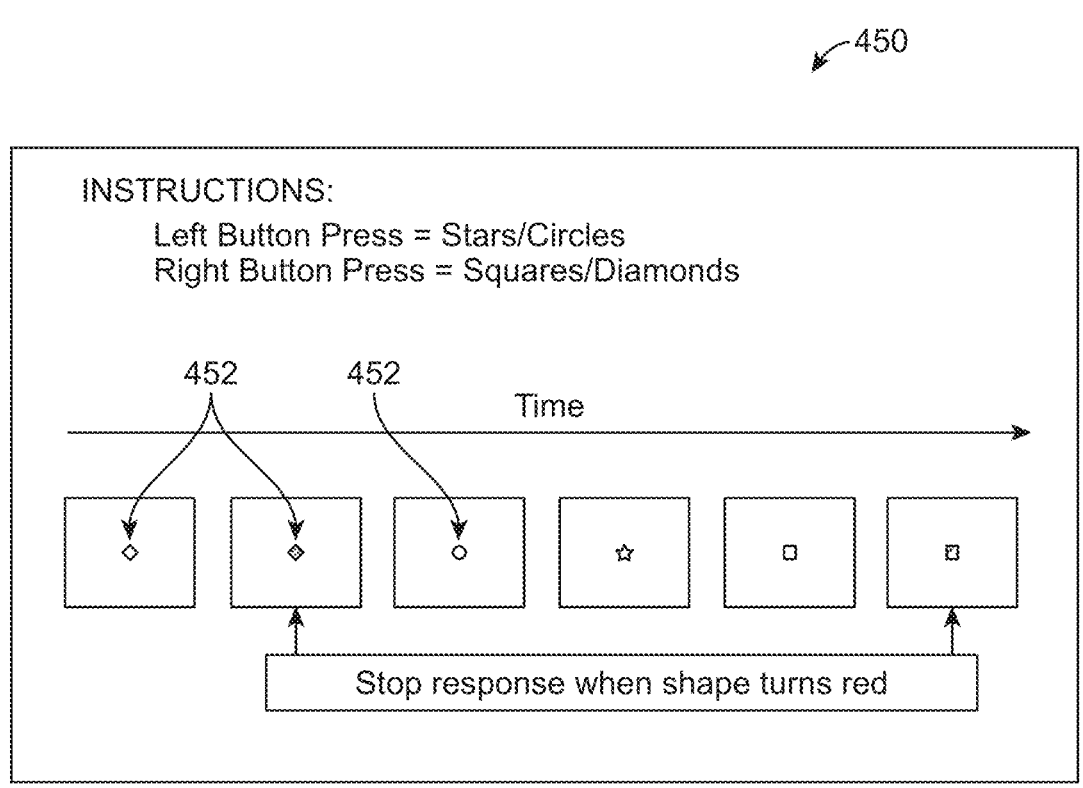
FIG. 21 shows an exemplary screenshot of a stop-signal task, in accordance with embodiments.

FIG. 21 shows an exemplary screenshot of a stop-signal task 450 for evaluating the speed of initiating and inhibition action to visual cues in the environment. Subjects may be instructed to issue a speeded left or right hand button press based on a predetermined mapping that links shape stimuli to either a left hand or a right hand response (e.g., circle or star=left button press; square or diamond=right button press). A series of shapes 452 may be presented one at a time, and subjects may be instructed to respond as fast and as accurately as possible to each shape. On 70% of trials, a shape may appear and disappear upon a response. On 30% of trials (i.e., stop-signal trials), a shape may appear, but then change color at some time interval after its onset. Subjects may be instructed to stop their response whenever a shape changes color. The time interval for stop-signals may adjust dynamically based on the subject's success or failure at stopping on the previous stop-signal trial, ultimately approximating a 50% success rate of stopping. Such a dynamic adjustment process be used to estimate an individual's stop-signal reaction time. The task instructions, practice trials, and performance trials can take approximately 5 minutes to complete.

The stimuli may comprise a small fixation point in the center of the screen. White shapes may appear one at a time in the same location as the fixation point. The background may be a dark gray color. Shapes may turn to a red color on stop-signal trials. Responses may be registered via a button press with the preferred hand on a response pad.

Subjects may respond to each shape that appears with a left or right button press. In total, they may complete a single block of 150 trials, 30% of which may be stop-signal trials. A variable inter-trial interval may be introduced between trials. Subjects may first complete a practice block of 30 trials. Subsequently, the subjects may complete a total of 150 performance trials.

Key dependent measures for the stop-signal task may comprise Go Reaction Time, Stop-Signal Reaction Time, and Post-Stop Slowing. Go Reaction Time may comprise the response latency to shapes that do not change color. Stop-Signal Reaction Time may comprise the estimated response latency to stop a reaction. Post-Stop Slowing may represent the slowing of reaction time following failed stop-signal trials.

Implicit Motor Sequence Task

An implicit motor sequence task may comprise another exemplary task that may be provided by the evaluation apparatus to evaluate cognitive processes related to memory and learning. The ability to form motor sequences rapidly and implicitly provides a significant advantage in skill acquisition. Additionally, when motor sequences are well established, disruption to their execution can be detrimental to performance and recovery of performance. The implicit motor sequence task as described herein can measure individual differences in the efficiency of learning a repeated sequence of motor actions, the costs to performance when the learned sequence is disrupted, and the skill at re-acquiring the sequence upon its reinstatement.

Figure 22:
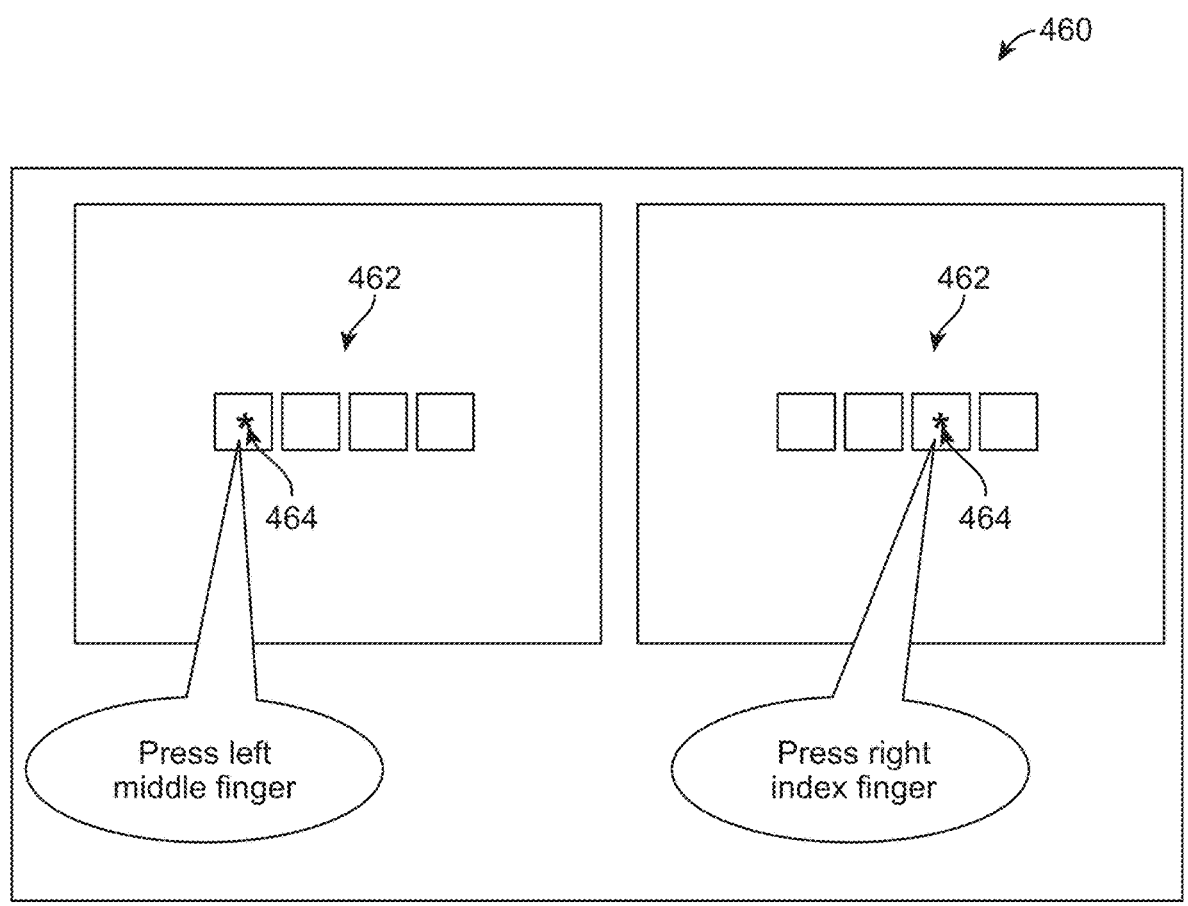
FIG. 22 shows an exemplary screenshot of an implicit motor sequence task, in accordance with embodiments.

FIG. 22 shows an exemplary screenshot of an implicit motor sequence task 460 for evaluating the ability to form motor sequences rapidly and implicitly. Subjects may be presented with a horizontal array 462 of 4 open squares, wherein each square may be mapped to a response finger such that that the two left-most squares map to the left hand middle and index fingers and the two right-most squares map to the right hand index and middle fingers, respectively. A series of asterisks 464 may appear one at a time in one of the four squares, and the subject may be instructed to press the corresponding response button. In the initial block of trials, the series of asterisks appear may randomly and equiprobably across the four squares. Next, several blocks of trials may be presented in which asterisks appear in a repeated pattern across the four squares. A subsequent block of trials may then presents a random order of asterisk placement, followed by a block of trials in which the repeated pattern is reinstated. The task can measure acquisition of the sequential motor pattern, the costs to performance when the sequence is disrupted, and the degree of recovery in performance when the sequence is then reinstated. The task instructions, practice trials, and performance trials may take approximately 8 minutes to complete.

The stimuli may comprise four white-outlined squares aligned in a horizontal array, equally spaced. The center of the squares and background may be dark gray. A white asterisk may be presented in one of the squares at a time. Responses may be registered via button presses with both hands on the response pad.

Each block of trials may begin with presentation of an asterisk in a box until a response is issued. After a response is issued, a fixed inter-trial interval may transpire and the next asterisk may appear in a box. Each block may contain 80 total asterisk presentation trials. The first block of trials may involve distribution of the asterisks equally and randomly across the four boxes. Blocks 2-5 may each present a 10-sequence pattern 8 times. Block 6 may involve a random presentation similar to Block 1, and Block 7 may present the 10-sequence pattern presented in Blocks 2-5. Subjects may first complete a practice block of 20 trials. Subsequently, the subjects may complete a total of 7 blocks of 80 performance trials as described above.

Key dependent measures for the implicit motor sequence task may comprise learning of sequential motor patterns, reaction time and accuracy costs to random blocks, and percentage recovery of reaction time and accuracy following random blocks.

Motor Timing and Rhythm Task

A motor timing and rhythm task may comprise another exemplary task that may be provided by the evaluation apparatus to evaluate cognitive processes related to command and control. Matching and maintaining rhythmic motor actions can be critical to performance in many situations. Individuals sometimes need to optimize performance by matching their motor actions to rhythmic cues provided in the environment or by executing a rhythmic timing of sequential motor actions using an internal (i.e., mental) representation of a rhythmic motor sequence. The motor timing and rhythm task as described herein can measure individual differences in the accuracy of externally cued rhythmic motor timing and rhythmic motor timing that is maintained on the basis of an internal, mental representation.

Figure 23:
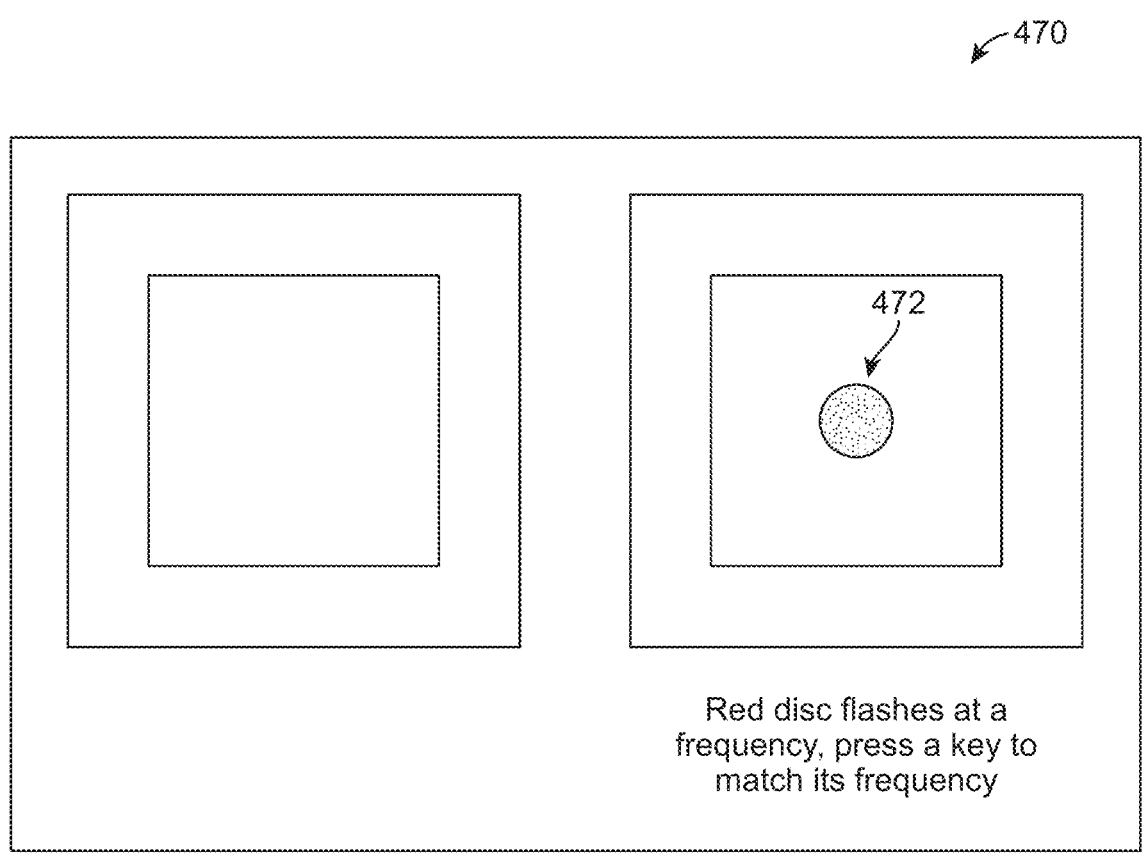
FIG. 23 shows an exemplary screenshot of a coincident timing task, in accordance with embodiments.

FIG. 23 shows an exemplary screenshot of a coincident timing task 470 for evaluating the ability to match and maintain rhythmic motor actions. Subjects may be presented with an image of a small circular disc 472 that flashes on a computer screen at a repeated rhythm (i.e., frequency). Subjects may be instructed to time their taps a response button to match the rhythm of the circle flashes as accurately as possible. Several repetitions of the rhythm may be presented, and then the screen may turn blank while the subject continues to tap the response button to the same rhythm (but now without the visual cue). After a certain number of trials, the subject may be given a new rhythm to match. The task instructions, practice trials, and performance trials may take approximately 5 minutes to complete.

The stimulus may comprise a single circular disc flashing in the center of the screen according to a predetermined rhythm. Responses may be registered by a button press with the preferred hand on the response pad.

Subjects may be presented with a circular disc flash on the screen in a repeated rhythm. They may be instructed to match their button press to the circular disc onsets, thus matching the rhythmic pattern. The disc may disappear after a fixed number of trials while subjects continue to maintain the established rhythm for a fixed number of rhythm repetitions. Subjects may complete several trials involving different rhythmic sequences. Subjects may first complete a practice block of trials, then complete a series of performance trials.

The key dependent measure for the motor timing and rhythm task may comprise accuracy, which may be defined as the absolute error calculated as the difference between the true rhythm and actual rhythm produced by the subject.

Risk-Taking Task

A risk-taking task may comprise another exemplary task that may be provided by the evaluation apparatus to evaluate cognitive processes related to command and control. Performing in dynamic, reaction situations invites opportunities to take risks or be cautious in decision-making. Individuals vary in their tendencies and preferences toward making risky versus cautious decisions when outcomes are at stake. The risk-taking task as described herein can measure individual differences in the preference for making risky versus more cautious decisions when rewards are at stake.

Figure 24:
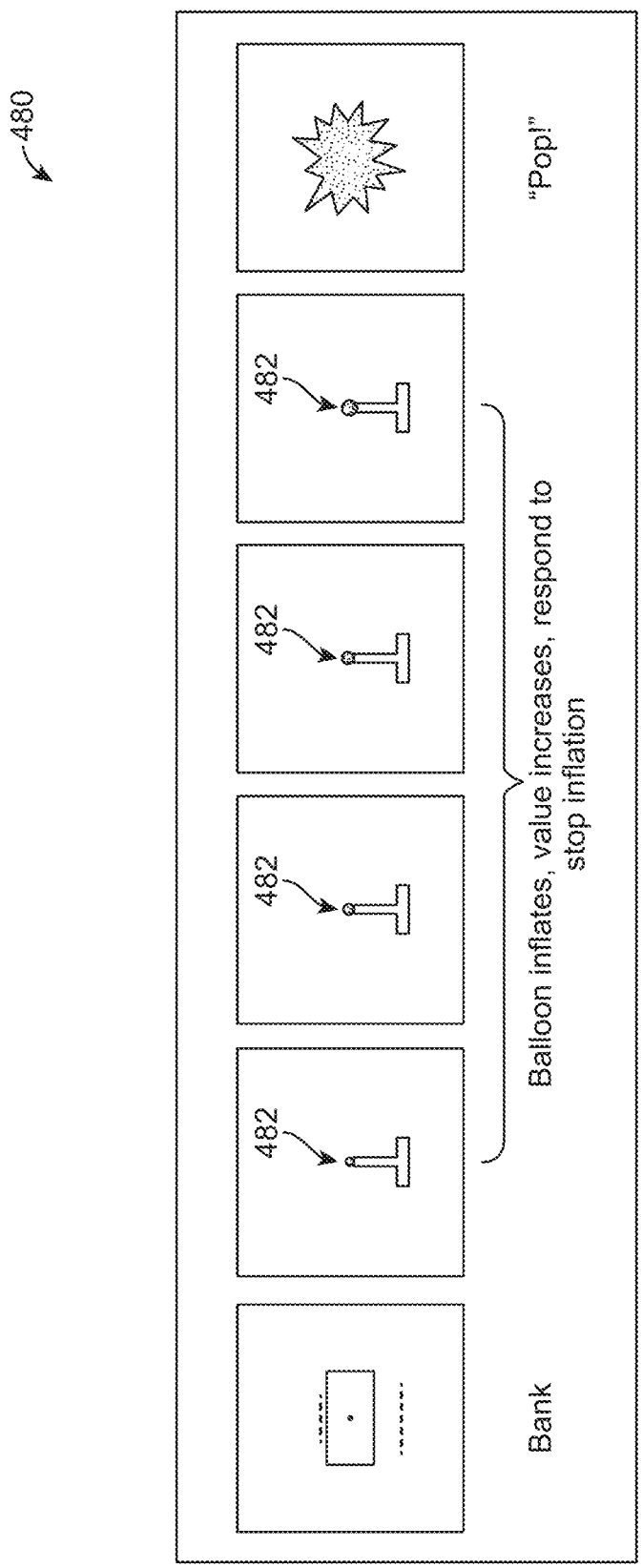
FIG. 24 shows an exemplary screenshot of a risk-taking task, in accordance with embodiments.

FIG. 24 shows an exemplary screenshot of a risk-taking task 480 for evaluating preference for making risky versus more cautious decisions. Subjects may be presented with a small balloon 482 in the center of the screen. The balloon may begin inflating, one inflation at a time, and with each inflation, the subject may earn points. Subjects may be instructed to maximize their point earnings. Each inflation may lead to a visible increase in the size of the balloon, wherein the subject's points increase by a fixed amount with each increase in size of the balloon. Each inflation may also associated with a risk of the balloon popping. If the balloon pops with any inflation, the accumulated points for that balloon are lost. Subjects are free to choose how much to let the balloon inflate, or can stop inflations and cash out the points by pressing a response key. The task instructions, practice trials, and performance trials may take approximately 5 minutes to complete.

The stimuli may comprise a balloon that appears in the center of the screen at an initial, starting circumference and diameter, and then begins to inflate. A subject may stop the balloon from further inflations by pressing a response key. Stopping the balloon inflations can be registered via a button press with the preferred hand on the response pad.

Subjects may inflate a single series of balloons in an effort to acquire as many points as possible. Subjects may first complete a practice block of trials, then complete a single block of performance trials.

The key dependent measure for the risk-taking task may comprise adjusted average inflations, which may be defined as the average number of balloon inflations adjusted for the pop trials.

Angle Prediction Task

An angle prediction task may comprise another exemplary task that may be provided by the evaluation apparatus to evaluate cognitive processes related to visual perception. Performing in dynamic visual environments can place high demands on the ability to predict the angle at which a moving target is moving or the angle that a moving target will take after ricocheting off of another object. The angle prediction task as described herein can measure individual differences in the accuracy of predicting how a moving target will angle off of stationary objects.

Figure 25:
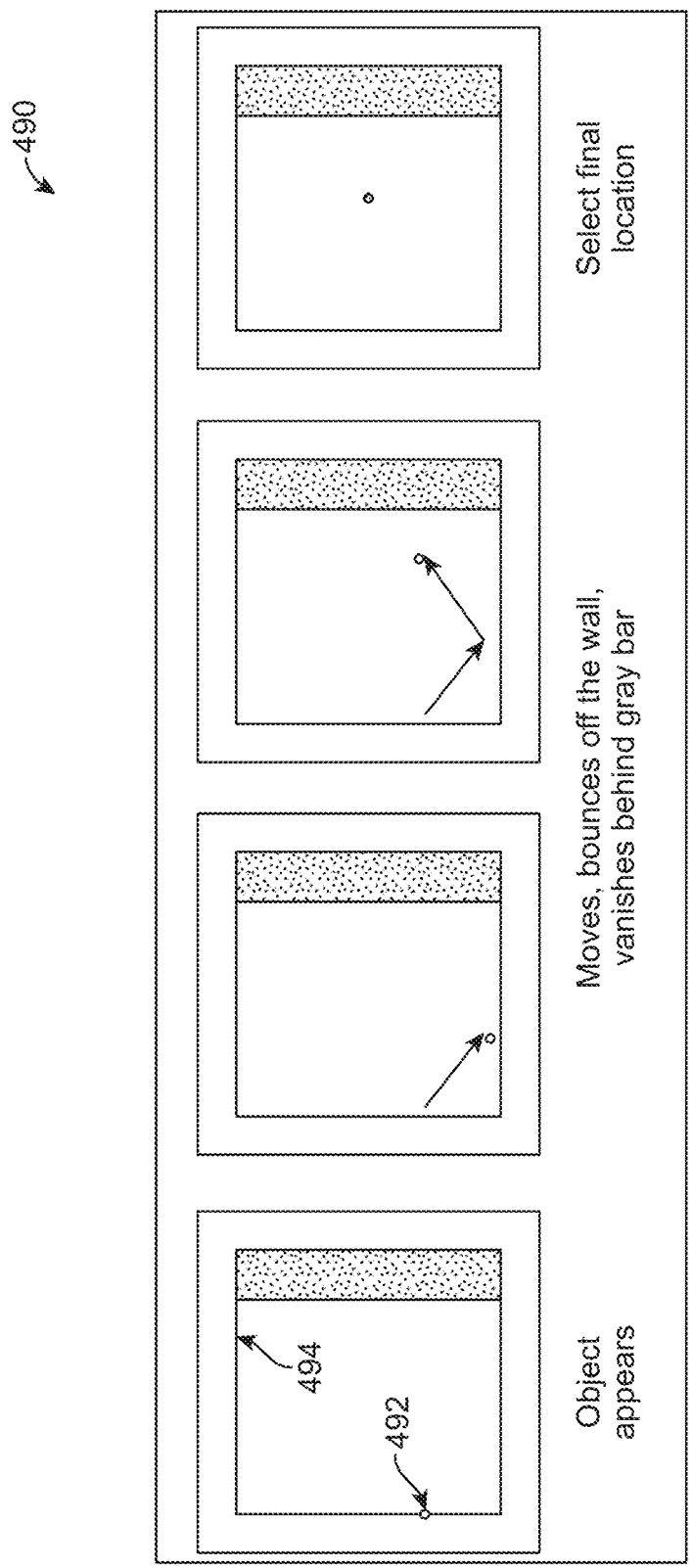
FIG. 25 shows an exemplary screenshot of an angle prediction task, in accordance with embodiments.

FIG. 25 shows an exemplary screenshot of an angle prediction task 490 for evaluating the ability predict how a moving target will angle off of stationary objects. A small ball 492 may appear along one side of a rectangular box 494 and immediately move toward an adjoining side of the box. At the point of intersection with the adjoining side, the ball may disappear, but the subject may be instructed that the ball continues to move. The subject may be instructed to use the angle of the initial moving ball to predict where the ball would hit the second, third, or fourth side of the box. The task instructions, practice trials, and performance trials may take approximately 5 minutes to complete.

The stimulus may be a small white ball that can appear next to any side of the rectangular box. Subject responses may be registered by a mouse click at the preferred target intersection point.

Subjects may be presented with a large white rectangular frame against a black background. A ball may appear at some position next to one of the sides and begin moving toward an adjoining side within the box. Upon hitting the adjoining side, the ball may disappear. Subjects may use the angle of the initial ball movement to predict when the ball would strike either the second, third, or fourth sides of the rectangular frame. Subjects may first complete a practice block of 4 trials, then complete a single block of performance trials.

The key dependent measure for the angle prediction task may comprise accuracy, defined as the spatial error of the prediction.

Angle Estimation Task

An angle estimation task may comprise another exemplary task that may be provided by the evaluation apparatus to evaluate cognitive processes related to visual perception. Performing in dynamic visual environments can place high demands on the ability to estimate spatial angles. The angle estimation task as described herein can measure individual differences in the accuracy of estimating a spatial angle.

Figure 26:
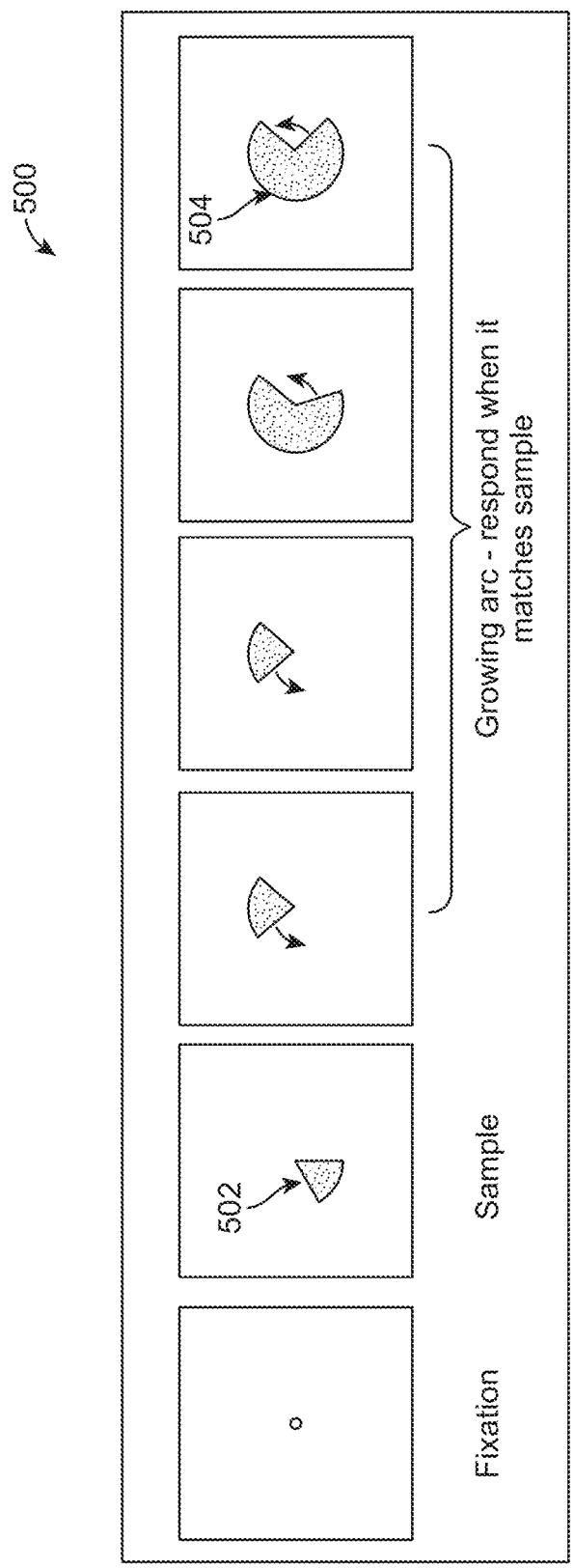
FIG. 26 shows an exemplary screenshot of an angle estimation task, in accordance with embodiments.

FIG. 26 shows an exemplary screenshot of an angle estimation task 500 for evaluating the ability to estimate spatial angles. The task may require a subject to estimate angles within a circle. The subject may be presented with a brief presentation of a pie slice 502 of a circle 504. The slice may be less than 180 degrees, and subject may be instructed to maintain this angle in mind. The slice may then disappear, and a new circle may begin to fill in a counter-clockwise manner. The subject may be instructed to stop the filling circle to match the pie slice previously viewed. The task instructions, practice trials, and performance trials may take approximately 5 minutes to complete.

The stimuli may comprise red pie slices angling less than 180 degrees. Responses to stop the filling of a circle to match the initially presented pie slice may be registered by a button press with the preferred hand on the response pad.

Subjects may be presented with one pie slice at a time and then asked to estimate the angle of that slice by stopping a filling circle at that angle. Next, a new pie slice angle may be presented. The angles may be predetermined and presented in a fixed order to prevent trial-by-trial confounds. Subjects may first complete a practice block of 4 trials, then complete a single block of performance trials.

The key dependent measure for the angle estimation task may comprise accuracy, which may be defined as the absolute angular error calculated across trials.

Tasks to evaluate cognitive processes related to command and control may further include a motor prediction and adjustment task. Performing in reactive and dynamic visual environments often requires split-second adjustments to predictions about how to react to intersect a moving target. A motor prediction and adjustment task can measure individual differences in the skill at predicting an initial reaction to intersect a moving target as well as adjusting this prediction and reaction when the target unexpectedly changes direction.

Tasks to evaluate cognitive processes related to memory and learning may further include a memory suppression task. Performance stability often requires that recent mistakes, errors, or failures be intentionally forgotten so as to not interfere with subsequent performance. A memory suppression task can measure individual differences in the ability to suppress memories and limit their intrusion on and interference with subsequent performance.

In addition to the tasks described herein, speed-accuracy balance of a subject, or the subject's performance tendencies across a set of speeded reaction time tasks, may be used as a global measure a subject's ability to regulate and optimize the speed and accuracy of reaction.

The evaluation apparatus as described herein may be configured to provide a custom combination of one or more tasks described herein, in order to suit a particular application of the evaluation apparatus. The tasks provided by the evaluation apparatus may belong to one or more of broad domains corresponding to visual perception, memory and learning, and/or command and control as described herein.

An evaluation apparatus may be configured to provide evaluations of football players. The apparatus may provide a customized set of tasks to assess broad categories of field vision skills, play recognition skills, and command and control skills. The field vision skills category may include a speeded target detection task, rapid visual attention task, multiple object tracking task, and/or dynamic motion detection task as described herein. The play recognition skills category may include a visual pattern recognition task, action learning task, and/or response alternatives task as described herein. The command and control skills may comprise an impulse control task, distraction control task, motion compatibility task, and/or speed-accuracy balance assessment as described herein.

An evaluation apparatus may be configured to provide evaluations of baseball or softball players. The apparatus may provide a customized set of tasks to assess broad categories of visual cognitive skills, recognition skills, and command and control skills. The visual cognitive skills category may include a speeded target detection task, rapid visual attention task, target movement discrimination task, and/or trajectory estimation task as described herein. The recognition skills category may include a visual change detection task and/or action learning task as described herein. The command and control skills category may include an impulse control task, motion compatibility task, coincident timing task, and/or coincident disjunctive task as described herein.

An evaluation apparatus may be configured to provide evaluations of basketball players. The apparatus may provide a customized set of tasks to assess broad categories of court vision, play recognition skills, and command and control skills. The court vision category may include a speeded target detection task, rapid visual attention task, and/or multiple object tracking task as described herein. The play recognition skills category may include a visual change detection task, action learning task, and/or response alternatives task as described herein. The command and control skills category may include an impulse control task, distraction control task, motion compatibility task, and/or coincident disjunctive task as described herein.

An evaluation apparatus may be configured to provide evaluations of hockey players. The apparatus may provide a customized set of tasks to assess broad categories of ice vision, play recognition skills, and command and control skills. The ice vision category may include a speeded target detection task, rapid visual attention task, multiple object tracking task, and/or dynamic motion detection task as described herein. The play recognition skills category may include a visual change detection task, action learning task, and/or response alternatives task as described herein. The command and control skills category may include an impulse control task, distraction control task, motion compatibility task, and/or coincident timing task as described herein.

An evaluation apparatus may be configured to provide evaluations of military personnel. The apparatus may provide a customized set of tasks to assess broad categories of visual cognitive skills, memory and learning skills, and command and control skills. The visual cognitive skills category may include a speeded target detection task, rapid visual attention task, multiple object tracking task, and/or dynamic motion detection task as described herein. The memory and learning skills category may include a visual pattern recognition task, visual change detection task, action learning task, and/or response alternatives task as described herein. The command and control skills category may include an impulse control task, distraction control task, motion compatibility task, and/or coincident timing task as described herein.

An evaluation apparatus may be configured to provide evaluations of individuals having, suspected of having, or recovering from having a concussion. The apparatus may provide a customized set of tasks to assess broad categories of visuoperceptive cognitive skills, memory and learning skills, and command and control skills. The visuoperceptive cognitive skills category may include a speeded target detection task, rapid visual attention task, and/or multiple object tracking task as described herein. The memory and learning skills category may include a visual change detection task, action learning task, and/or response alternatives task as described herein. The command and control skills category may include an impulse control task, distraction control task, and/or motion compatibility task as described herein.

Figure 27:
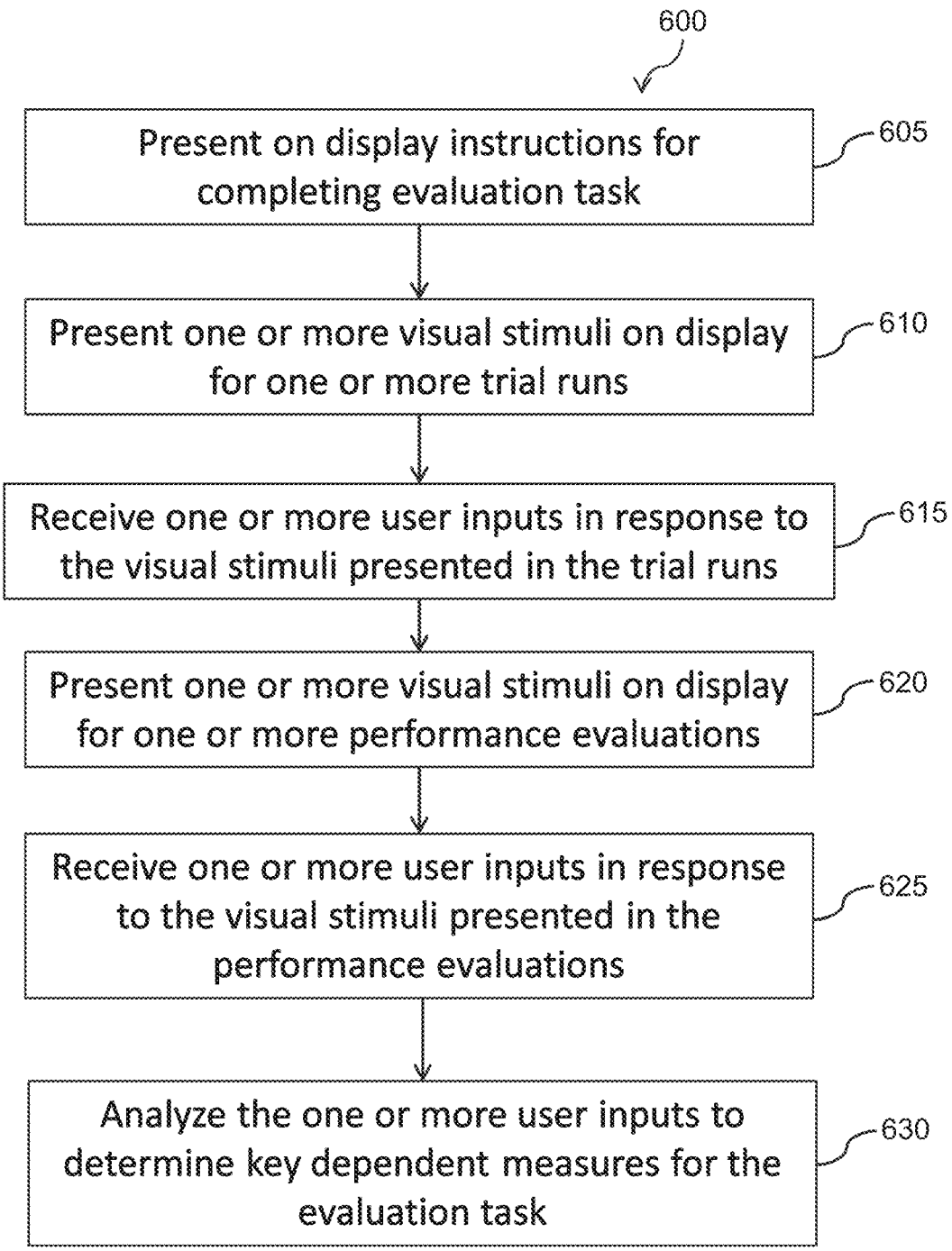
FIG. 27 illustrates an exemplary method of evaluating a subject using an evaluation apparatus as described herein.

FIG. 27 illustrates a method 700 of evaluating a subject using an evaluation apparatus as described herein. The method 600 may be performed with a user interface provided on a computing device, the computing device comprising a display and the user interface for receiving user input in response to the instructions provided on the display (e.g., a response pad as described herein). At step 605, instructions for completing an evaluation task may be presented to a subject on a display. At step 610, one or more visual stimuli corresponding to the evaluation task may be presented to the subject via the display for one or more trial runs. At step 615, one or more user inputs in response to the visual stimuli presented in the trial runs may be received, for example via one or more user input devices such as a computer keyboard, mouse, or a response pad as described herein. Optionally, user inputs may be analyzed to confirm that the subject is correctly following the instructions for the evaluation task. At step 620, one or more visual stimuli corresponding to the task may be presented to the subject via the display for one or more performance evaluations. At step 625, one or more user inputs in response to the visual stimuli presented in the performance evaluations may be received via one or more user input devices as described herein. At step 630, the one or more user inputs in response to the visual stimuli may be analyzed to determine one or more key dependent measures corresponding to the evaluation task, as described herein. Optionally, if the evaluation procedure comprises a plurality of evaluation runs, analyzed key dependent measures from one run may be used to adjust the visual stimuli presented to the subject during the next evaluation run, such that the presented stimuli are dynamically adjusted to the subject throughout the evaluation.

Although the above steps show an exemplary a method 600 of evaluating one or more cognitive processes of a subject, a person of ordinary skill in the art will recognize many variations based on the teachings described herein. The steps may be completed in a different order. Steps may be added or deleted. Some of the steps may comprise sub-steps of other steps. Many of the steps may be repeated as often as desired by the user.

Figure 28:
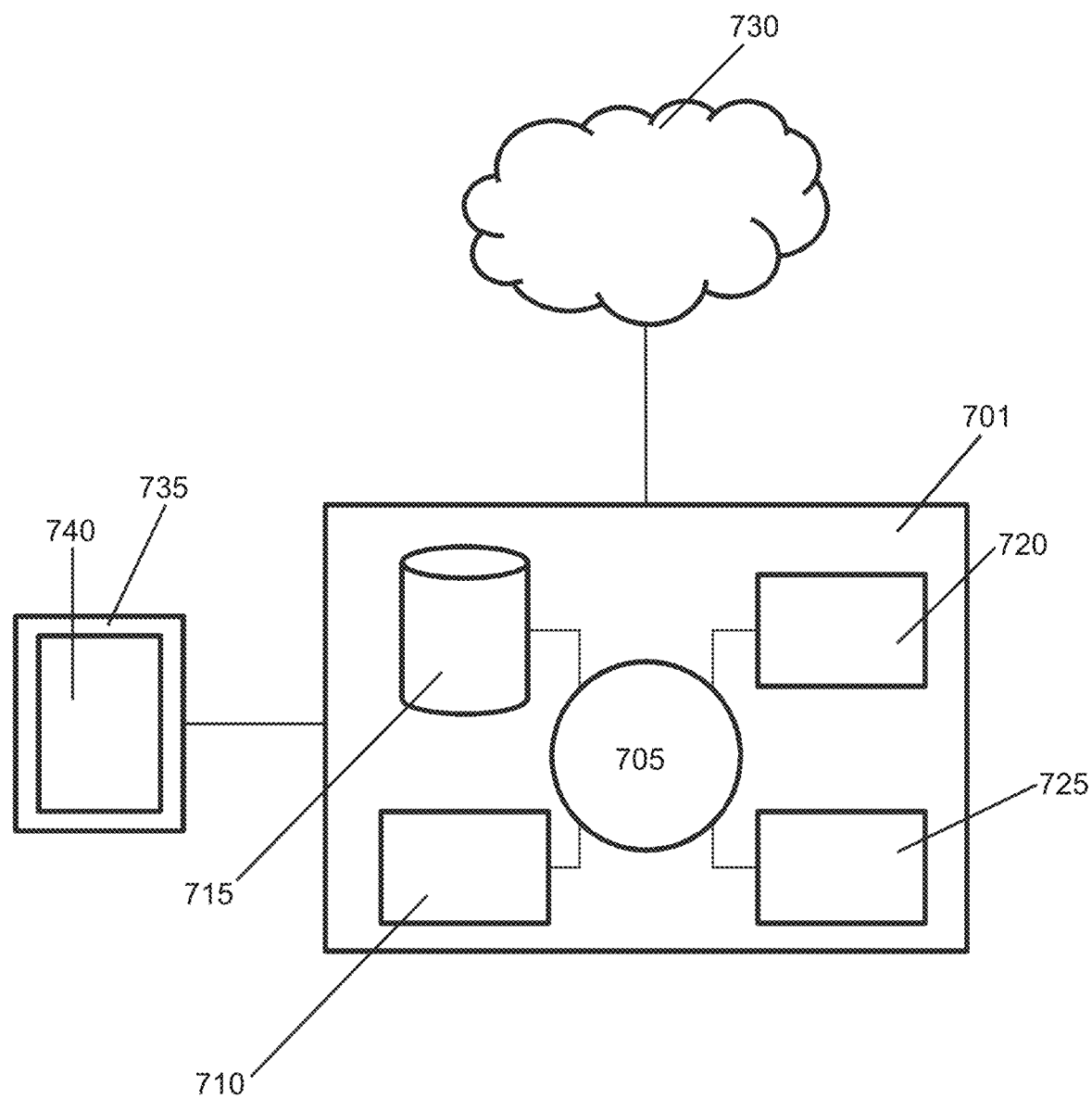
FIG. 28 shows a computer system suitable for incorporation with the methods and apparatus described herein.

The present disclosure provides computer control systems that are programmed to implement methods of the disclosure. FIG. 28 shows a computer system 701 suitable for incorporation with the methods and apparatus described herein. The computer system 701 can process various aspects of information of the present disclosure, such as, for example, the various visual stimuli, user inputs in response to the stimuli, and the key dependent measures determined based on the user inputs. The computer system 701 can be an electronic device of a user or a computer system that is remotely located with respect to the electronic device. The electronic device can be a mobile electronic device.

The computer system 701 includes a central processing unit (CPU, also "processor" and "computer processor" herein) 705, which can be a single core or multi core processor, or a plurality of processors for parallel processing. The computer system 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The computer system 701 can be operatively coupled to a computer network ("network") 730 with the aid of the communication interface 720. The network 730 can be the Internet, an internet and/or extranet, or an intranet and/or extranet that is in communication with the Internet. The network 730 in some cases is a telecommunication and/or data network. The network 730 can include one or more computer servers, which can enable distributed computing, such as cloud computing. The network 730, in some cases with the aid of the computer system 701, can implement a peer-to-peer network, which may enable devices coupled to the computer system 701 to behave as a client or a server.

The CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and writeback.

The CPU 705 can be part of a circuit, such as an integrated circuit. One or more other components of the system 701 can be included in the circuit. In some cases, the circuit is an application specific integrated circuit (ASIC).

The storage unit 715 can store files, such as drivers, libraries and saved programs. The storage unit 715 can store user data, e.g., user preferences and user programs. The computer system 701 in some cases can include one or more additional data storage units that are external to the computer system 701, such as located on a remote server that is in communication with the computer system 701 through an intranet or the Internet.

The computer system 701 can communicate with one or more remote computer systems through the network 730. For instance, the computer system 701 can communicate with a remote computer system of a user (e.g., a parent). Examples of remote computer systems and mobile communication devices include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 701 with the network 730.

Methods as described herein can be implemented by way of machine (e.g., computer processor) executable code stored on an electronic storage location of the computer system 701, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 810 for ready access by the processor 705. In some situations, the electronic storage unit 715 can be precluded, and machine-executable instructions are stored on memory 710.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 701 can include or be in communication with an electronic display 735 that comprises a user interface (UI) 740 for providing, for example, instructions for completing a task, visual stimuli, user inputs, and analysis results. Examples of UI's include, without limitation, a graphical user interface (GUI) and web-based user interface.

Methods and systems of the present disclosure can be implemented by way of one or more algorithms and with instructions provided with one or more processors as disclosed herein. An algorithm can be implemented by way of software upon execution by the central processing unit 705.

Each of the examples as described herein can be combined with one or more other examples. Further, one or more components of one or more examples can be combined with other examples.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus comprising:
   a display to present a plurality of stimuli to a subject, wherein the plurality of stimuli comprises stimuli to measure visual perception of the subject, stimuli to measure memory and learning of the subject and stimuli to measure command and control of the subject; and
   a processor coupled to the display, the processor comprising instructions to determine the visual perception of the subject, the memory and learning of the subject, and the command and control of the subject and wherein the processor comprises instructions to provide an assessment task configured to measure an ability of the subject to act or withhold action, based on presenting a moving visual target and a point in space to the subject and measuring a speed and an accuracy of a response input from the subject deciding that the moving visual target is predicted to intercept the point in the space and the speed and the accuracy of the subject withholding the response input when the moving visual target is not predicted to intercept the point in the space.

2. The apparatus of claim 1, wherein the stimuli to measure visual perception of the subject comprises a plurality of stimuli to evaluate one or more of visual, visuoperceptual, or visual attention brain circuitries.

3. The apparatus of claim 1, wherein the plurality of stimuli comprise stimuli to evaluate one or more brain circuitries of an occipital cortex, fusiform gyrus, dorsal visual pathway, ventral visual pathway, parietal cortex, or visual association cortex of the subject.

4. The apparatus of claim 1, wherein the processor comprises instructions to provide a second assessment task configured to measure a speed and accuracy of the subject at locating a target in a distracting visual environment.

5. The apparatus of claim 1, wherein the processor comprises instructions to provide a second assessment task configured to measure an ability of the subject to track multiple moving targets simultaneously.

6. The apparatus of claim 1, wherein the processor comprises instructions to provide a second assessment task configured to measure a speed at which the subject disengages and shifts visual attention to a new target.

7. The apparatus of claim 1, wherein the processor comprises instructions to provide a second assessment task configured to measure an ability of the subject to detect a direction of movement of a target amid visual distraction and chaos.

8. The apparatus of claim 1, wherein the processor comprises instructions to provide a second assessment task configured to measure an ability of the subject to estimate a speed and trajectory of the moving visual target.

9. The apparatus of claim 1, wherein the processor comprises instructions to provide a second assessment task configured to measure an ability of the subject to rapidly discriminate a motion of the moving visual target.

10. The apparatus of claim 1, wherein the stimuli to measure memory and learning of the subject comprises a plurality of stimuli to evaluate one or more of explicit memory of the subject, implicit memory of the subject, or procedural memory of the subject.

11. The apparatus of claim 1, wherein the plurality of stimuli comprise stimuli to evaluate one or more brain circuitries of a hippocampus, parietal cortex, mesial temporal lobes, frontal lobes, or basal ganglia of the subject.

12. The apparatus of claim 1, wherein the processor comprises instructions to provide a second assessment task configured to measure an ability of the subject to recognize and discriminate complex visual patterns.

13. The apparatus of claim 1, wherein the processor comprises instructions to provide a second assessment task configured to measure an ability of the subject to detect subtle changes in a visual scene.

14. The apparatus of claim 1, wherein the processor comprises instructions to provide a second assessment task configured to measure an ability of the subject to learn how to react to new visual information based on probabilistic feedback.

15. The apparatus of claim 1, wherein the processor comprises instructions to provide a second assessment task configured to measure a speed and accuracy of the subject at selecting an optimal response for a situation as response options increase in number.

16. The apparatus of claim 1, wherein the processor comprises instructions to provide a second assessment task configured to measure a speed and accuracy of the subject at translating visual motion into action based on context.

17. The apparatus of claim 1, wherein the stimuli to measure command and control of the subject comprises a plurality of stimuli to evaluate one or more executive cognitive control systems of the subject.

18. The apparatus of claim 1, wherein the plurality of stimuli comprises stimuli to evaluate one or more brain circuitries of a dorsolateral and ventrolateral prefrontal cortex, motor cortex, premotor cortex, pre-supplementary motor cortex, parietal cortex, cingulate cortex, or subcortical basal ganglia structures of the subject.

19. The apparatus of claim 17, wherein the processor comprises instructions to measure an ipsilateral response to a stimulus shown on a first side of the display and a contralateral response to the stimulus shown on a second side of the display, the first side separated from the second side with a midline of the display when a midline of the subject is aligned with the midline of the display.

20. The apparatus of claim 19, wherein a right stimulus is presented on a right side of the display and the subject responds with a right hand to measure the ipsilateral response and wherein a left stimulus is presented on a left side of the display and the subject responds with the right hand to measure the contralateral response, and wherein a time from presentation of the right stimulus to the subject providing an input with the right hand determines the ipsilateral response and wherein a time from presentation of the left stimulus to the subject providing an input with the right hand determines the contralateral response.

21. The apparatus of claim 19, wherein a left stimulus is presented on a left side of the display and the subject responds with a left hand to measure the ipsilateral response and wherein a right stimulus is presented on a right side of the display and the subject responds with the left hand to measure the contralateral response and wherein a time from presentation of the left stimulus to the subject providing an input with the left hand determines the ipsilateral response and wherein a time from presentation of the right stimulus to the subject providing an input with the left hand determines the contralateral response.

22. The apparatus of claim 1, wherein the processor comprises instructions to provide a second assessment task configured to measure an ability of the subject to regulate and optimize a speed and accuracy of reactions.

23. The apparatus of claim 1, wherein the processor comprises instructions to provide a second assessment task configured to measure an ability of the subject to prevent and recover from initial action impulses in response to the plurality of stimuli.

24. The apparatus of claim 1, wherein the processor comprises instructions to provide a second assessment task configured to measure an ability of the subject to minimize performance costs to reacting to the plurality of stimuli when faced with visual distractions.

25. The apparatus of claim 1, wherein the processor comprises instructions to provide a second assessment task configured to measure an ability of the subject to control the subject's timing of reactions to rapidly moving visual targets.

26. The apparatus of claim 1, wherein the processor comprises instructions to provide a second assessment task configured to measure an ability of the subject to encode and maintain representations of target locations in a working memory of the subject.

27. The apparatus of claim 1, wherein the processor comprises instructions to provide a second assessment task configured to measure a speed of initiation of action and inhibition of action by the subject in response to visual cues in an environment of the subject.

28. The apparatus of claim 1, wherein the processor comprises instructions to provide a second assessment task configured to measure an efficiency of the subject of learning a repeated sequence of motor actions, a detrimental effect on performance of the subject when the learned sequence is disrupted, and an ability of the subject to re-acquire the sequence upon reinstatement of the learned sequence after disruption.

29. The apparatus of claim 1, wherein the processor comprises instructions to provide a second assessment task configured to measure an accuracy of externally cued rhythmic motor timing of the subject and rhythmic motor timing of the subject that is maintained based on an internal, mental representation of the timing.

30. The apparatus of claim 1, wherein the processor comprises instructions to provide a second assessment task configured to measure a preference of the subject for making relatively risky decisions or relatively cautious decisions when rewards are at stake.

31. The apparatus of claim 1, wherein the processor comprises instructions to provide a second assessment task with the plurality of stimuli configured to measure an accuracy of the subject in predicting how the moving visual target will ricochet at an angle off of stationary objects.

32. The apparatus of claim 1, wherein the processor comprises instructions to provide a second assessment task configured to measure an accuracy of the subject in estimating a spatial angle from the plurality of stimuli.

33. The apparatus of claim 1, wherein the processor comprises instructions to provide a second assessment task configured to measure an ability of the subject to predict an initial reaction to intersect the moving visual target among the plurality of stimuli and an ability of the subject to adjust the initial reaction when the target unexpectedly changes direction.

34. The apparatus of claim 1, wherein the processor comprises instructions to provide a memory suppression task configured to measure an ability of the subject to suppress a recent mistake from interfering with subsequent performance of the subject in response to the plurality of stimuli.

35. The apparatus of claim 1, further comprising:
an input device configured to be responsive to one or more hands of the subject, the input device coupled to the processor;
wherein the processor comprises instructions to:
receive an instruction to show the plurality of stimuli on the display;
provide, within about 20 ms of receiving the instructions, the plurality of stimuli on the display; detect the subject providing the response input to the input device;
and measure, within about 20 ms of detecting the response input, a performance of the subject in performing the assessment task based on the response input provided to the input device.

36. The apparatus of claim 35, wherein the instructions comprise instructions of an application downloaded from a network, wherein the display comprises a display of a computing device, and wherein the input device is coupled to the computing device.

37. A method of evaluating performance of a subject, the method comprising:
providing a display to present a plurality of stimuli to the subject, wherein the plurality of stimuli comprises stimuli to measure visual perception of the subject, stimuli to measure memory and learning of the subject and stimuli to measure command and control of the subject;
providing a processor coupled to the display, the processor comprising instructions to determine the visual perception of the subject, the memory and learning of the subject, and the command and control of the subject, and instructions to provide an assessment task configured to measure an ability of the subject to act or withhold action, based on presenting a moving visual target and a point in space to the subject and measuring a speed and an accuracy of a response input from the subject deciding that the moving visual target is predicted to intercept the point in the space and the speed and the accuracy of the subject withholding the response input when the moving visual target is not predicted to intercept the point in the space: and
receiving, using an input device coupled to the processor, the response input provided by the subject in response to the plurality of stimuli.

* * * * *